United States Patent
Wang et al.

(10) Patent No.: US 9,502,730 B2
(45) Date of Patent: Nov. 22, 2016

(54) PRINTED BIOFUEL CELLS

(71) Applicant: The Regents of the University of California, Oakland, CA (US)

(72) Inventors: Joseph Wang, San Diego, CA (US); Joshua Ray Windmiller, Del Mar, CA (US);
(Continued)

(73) Assignee: The Regents Of The University Of California, Oakland, CA (US)

(*) Notice: Subject to any disclaimer, the term of this patent is extended or adjusted under 35 U.S.C. 154(b) by 179 days.

(21) Appl. No.: 14/362,100

(22) PCT Filed: Nov. 30, 2012

(86) PCT No.: PCT/US2012/067481
§ 371 (c)(1),
(2) Date: May 30, 2014

(87) PCT Pub. No.: WO2013/130145
PCT Pub. Date: Sep. 6, 2013

(65) Prior Publication Data
US 2014/0322617 A1    Oct. 30, 2014

Related U.S. Application Data

(60) Provisional application No. 61/625,655, filed on Apr. 17, 2012, provisional application No. 61/565,457, filed on Nov. 30, 2011.

(51) Int. Cl.
*H01M 8/16* (2006.01)
*H01M 4/90* (2006.01)
(Continued)

(52) U.S. Cl.
CPC ............. *H01M 8/16* (2013.01); *H01M 4/8807* (2013.01); *H01M 4/8832* (2013.01);
(Continued)

(58) Field of Classification Search
CPC .................. H01M 8/16; H01M 4/9008; H01M 4/8828
See application file for complete search history.

(56) References Cited

U.S. PATENT DOCUMENTS 7,368,190 B2    5/2008    Heller et al.
2005/0255345 A1*  11/2005   Gerritse et al. ..... H01M 4/8626
                                                          429/401
(Continued)

FOREIGN PATENT DOCUMENTS

WO    2011117357    9/2011

OTHER PUBLICATIONS

Arshak, K. et al., "Conducting polymers and their applications to biosensors: Emphasizing on foodborne pathogen dection", IEEE Sens. J. 2009, 9, 1942-1951.
(Continued)

*Primary Examiner* — Stewart Fraser
(74) *Attorney, Agent, or Firm* — Perkins Coie LLP

(57) ABSTRACT

Methods, systems, and devices are disclosed for implementing a biofuel cell device for extracting energy from a biofuel. In one aspect, a biofuel cell device includes a substrate, an anode including a catalyst to facilitate the conversion of a fuel in a biological fluid in an oxidative process that releases electrons captured at the anode, thereby extracting energy from the fuel substance, a cathode configured on the substrate adjacent to the anode and separated from the anode by a spacing region, and a load electrically coupled to the anode and cathode via electrical interconnects to obtain the extracted energy as electrical energy.

25 Claims, 19 Drawing Sheets

(72) Inventors: Wenzhao Jia, San Diego, CA (US)

(51) Int. Cl.
| | |
|---|---|
| *H01M 8/10* | (2016.01) |
| *H01M 8/02* | (2016.01) |
| *H01M 4/88* | (2006.01) |
| *H01M 4/92* | (2006.01) |
| *H01M 8/00* | (2016.01) |
| *H01M 8/04* | (2016.01) |

(52) U.S. Cl.
CPC ......... *H01M 4/8835* (2013.01); *H01M 4/9008* (2013.01); *H01M 8/0206* (2013.01); *H01M 8/0239* (2013.01); *H01M 8/0245* (2013.01); *H01M 8/1097* (2013.01); *A61B 2560/0214* (2013.01); *H01M 4/8803* (2013.01); *H01M 4/8846* (2013.01); *H01M 4/8853* (2013.01); *H01M 4/926* (2013.01); *H01M 8/004* (2013.01); *H01M 8/0247* (2013.01); *H01M 8/04208* (2013.01); *H01M 2250/30* (2013.01); *Y02B 90/18* (2013.01); *Y02E 60/522* (2013.01); *Y02E 60/527* (2013.01); *Y02P 20/136* (2015.11)

(56) References Cited

U.S. PATENT DOCUMENTS

| | | | | |
|---|---|---|---|---|
| 2005/0260492 | A1 | 11/2005 | Tucholski et al. | |
| 2006/0063043 | A1* | 3/2006 | Zeikus et al. | C12N 13/00 429/2 |
| 2008/0044721 | A1* | 2/2008 | Heller et al. | C12Q 1/26 429/2 |
| 2008/0160384 | A1* | 7/2008 | Iqbal et al. | H01M 4/8647 429/401 |
| 2010/0099010 | A1* | 4/2010 | Niessen et al. | H01M 6/34 429/506 |
| 2011/0135966 | A1* | 6/2011 | Jayaprakash | H01M 8/1023 429/2 |
| 2011/0274959 | A1* | 11/2011 | Bailey et al. | H01M 2/0257 429/124 |

OTHER PUBLICATIONS

Barton, S. C. et al., "Enzymatic biofuel cells for implantable and microscale devices", Chem. Rev. 2004, 104. 4867-4886.
Bedekar, A. S. et al., "Oxygen limitation in microfluidic biofuel cells", Chem. Eng. Commun. 2007, 195, 256-266.
Davis, F. et al., "Biofuel cells—recent advances and applications", Biosens. Bioelectron. 2007, 22, 1224-1235.
Gerard, M. et al., "Application of conducting polymers to biosensors", Biosens. Bioelectron. 2002, 17, 345-359.
Goldberg, H. D. et al., "Screen printing: A technology for the batch fabrication of integrated chemical-sensor arrays", Sens. Actuat. B 1994, 21, 171-183.
Kadara, R. O. et al., "Characterization and fabrication of disposable screen printed microelectrodes", Electrochem. Commun. 2009, 11, 1377-1380.
Kim, J. et al., "Challenges in biocatalysis for enzyme-based biofuel cells", Biotechnol. Adv. 2006, 24, 296-308.
Lee, D.W., Authorized Officer, Korean Intellectual Property Office, International Search Report, International Application No. PCT/US2012/067481, Nov. 8, 2013, 12 pages.
Metters, J.P. et al., "New directions in screen printed electroanalytical sensors: An overview of recent developments", Analyst 2011, 136, 1067-1076.
Moehlenbrock, M. J. et al., "Extended lifetime biofuel cells", Chem. Soc. Rev. 2008, 37, 1188-1196.
Parashkov, R. et al., "Large area electronics using printing methods", Proc. IEEE 2005, 93, 1321-1329.
Ramanavicius, A. et al., "Enzymatic biofuel cell based on anode and cathode powered by ethanol", Biosens. Bioelectron. 2008, 24, 761-766.
Rogers, J. A. et al., "Printing process suitable for reel-to-reel production of high-performance organic transistors and circuits", Adv. Mater. 1999, 11, 741-745.
Sattayasamitsathit, S. et al,, "Highly dispersed Pt nanoparticle-modified 3D porous carbon: a metallized carbon electrode material", Electrochem. Commun. 2011, 13, 856-860.
Smolander, M. et al., "Development of a printable laccase-based biocathode for fuel cell applications", Enzyme Microb. Tech., 2008, 43, 93-102.
Tudorache, M. et al., "Biosensors based on Screen-printing technology, and their applications in environmental and food analysis", Anal. Bioanal. Chem. 2007, 388, 565-578.
Wang, J. "Electrochemical glucose biosensors", Chem. Rev. 2008, 108, 814-825.
Yang, X. Y. et al., "Immobilization technology: A sustainable solution for biofuel cell design", Energy Environ. Sci. 2012, 5, 5540-5563.
Yu, E. H. et al., "Enzymatic biofuei cells—fabrication of enzyme electrodes", Energies 2010, 3, 23-42.
Zhou, M. et al., "A self-powered 'Sense-Act-Treat' system that is based on a biofuel cell and contoled by Boolean logic", Angew. Chem. Int. Ed. 2012, 51, 2686-2689.
Zhou, M. et al., "Biofuel cells for self-powered electrochemical biosensing and logic biosensing: a review", Electroanai. 2012, 24, 197-209.
Zhou, M. et al., "DNAzyme logic-controlled biofuel cells for self-powered biosensors", Chem. Commun. 2012, 48, 3815-3817.

\* cited by examiner

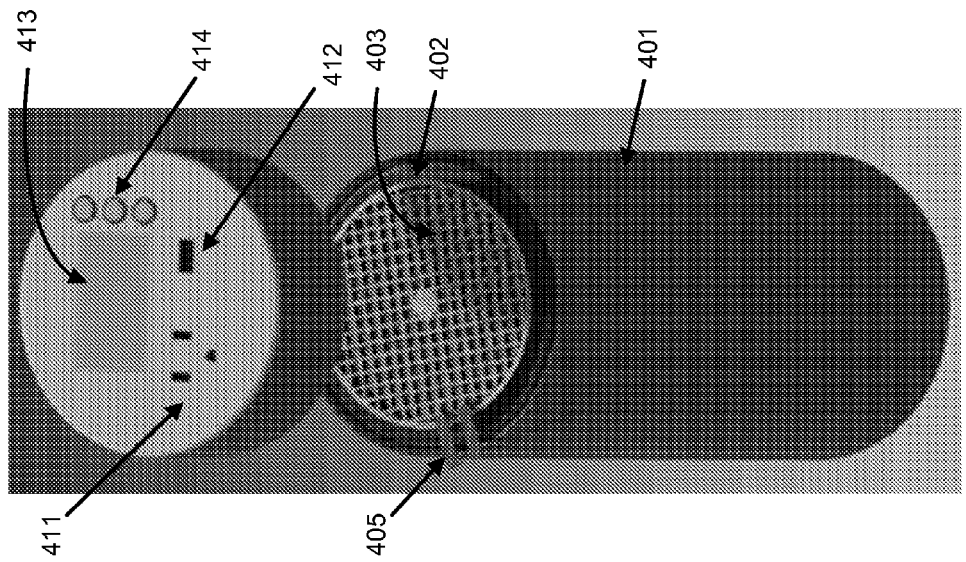
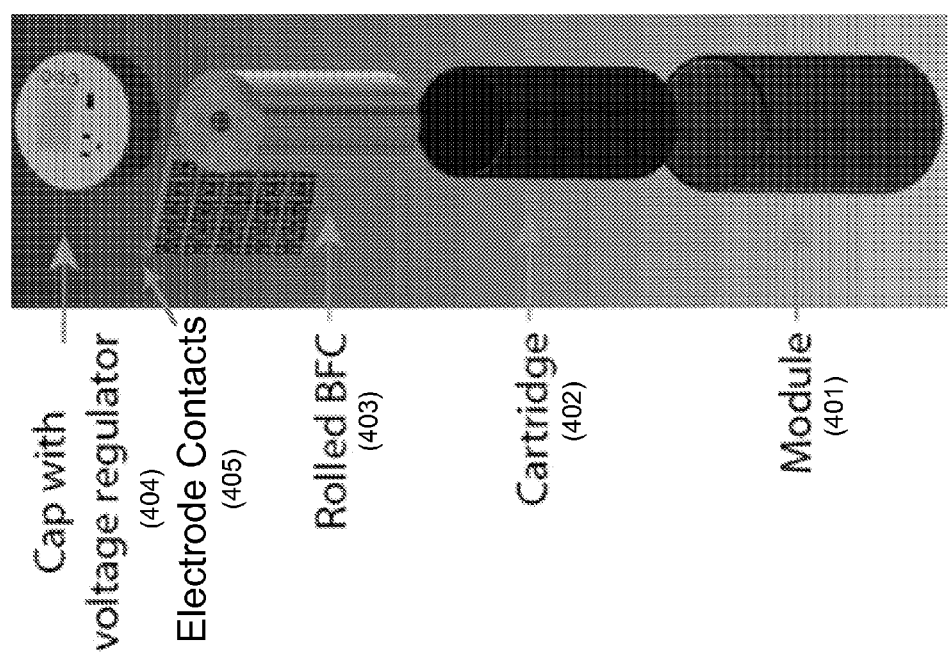
FIG. 4B
FIG. 4A

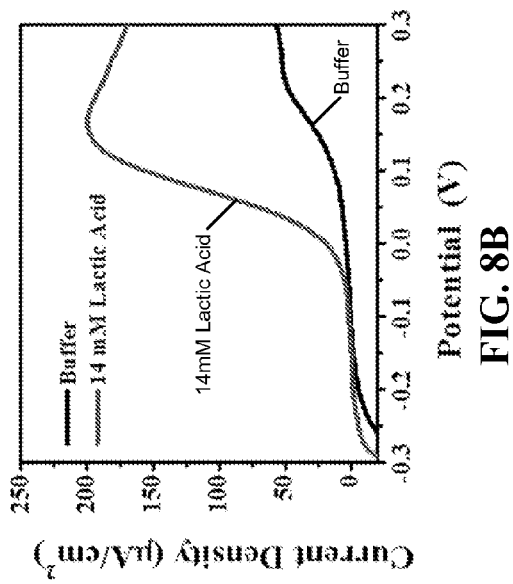
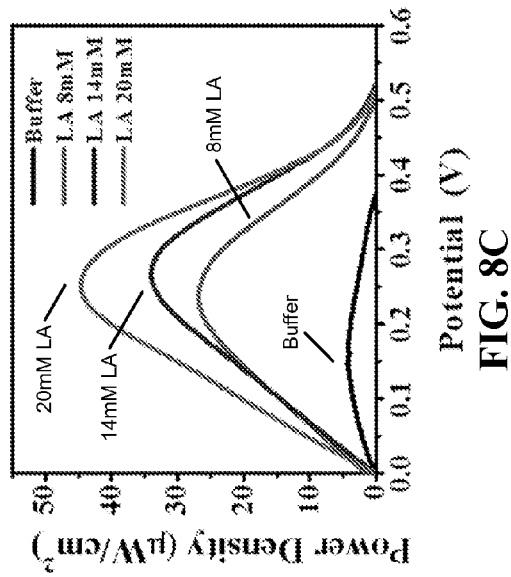
FIG. 8B
FIG. 8C
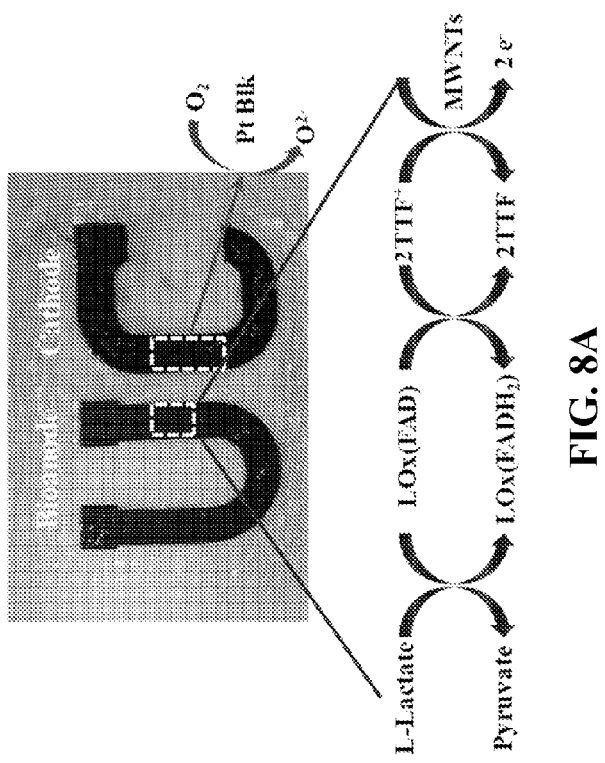
FIG. 8A

PRINTED BIOFUEL CELLS

CROSS REFERENCE TO RELATED APPLICATIONS

This patent document is a 35 USC §371 National Stage application of International Application No. PCT/US2012/067481 filed Nov. 30, 2012, which further claims the benefit of U.S. Provisional Patent Application No. 61/565,457, filed on Nov. 30, 2011, and U.S. Provisional Patent Application No. 61/625,655, filed on Apr. 17, 2012. The entire contents of the before-mentioned patent applications are incorporated by reference as part of the disclosure of this application.

STATEMENT REGARDING FEDERALLY SPONSORED RESEARCH OR DEVELOPMENT

This invention was made with government support under grants CBET-1066531 and CHE-1057562 awarded by the U.S. National Science Foundation (NSF) and the U.S. Department of Energy (DOE). The government has certain rights in the invention.

TECHNICAL FIELD

This patent document relates to fuel cell technologies.

BACKGROUND

A fuel cell is a device that converts chemical energy from a substance (e.g., referred to as a fuel) into electrical energy (e.g., electricity). Generally, the energy conversion includes a chemical reaction with oxygen or another oxidizing agent. For example, hydrogen is among a common fuel, and hydrocarbons such as natural gas and alcohols can also be used in fuel cells. For example, fuel cells differ from batteries in that they require a constant source of fuel and oxygen to operate, but can produce electricity continually provided the fuel and oxygen inputs are supplied to the fuel cell.

SUMMARY

Devices, systems, and techniques are disclosed for fabricating and implementing printed biofuel cells to extract energy from a biofuel.

In one aspect of the disclosed technology, a biofuel cell device includes a substrate, an anode formed on the substrate of an electrically conductive material, the anode including a catalyst to facilitate the conversion of a fuel substance in a biological fluid to a first product in an oxidative process that releases electrons captured at the anode, thereby extracting energy from the fuel substance, a cathode configured on the substrate adjacent to the anode and separated from the anode by a spacing region, the cathode formed of a material that is electrically conductive and capable of reducing an oxygenated substance in the biological fluid to a second product in a chemical reduction process in which the second product gains electrons, and a load configured as one or more electrical circuit elements electrically coupled between the anode and the cathode via electrical interconnects to obtain the extracted energy as electrical energy. Implementations of the biofuel cell device can optionally include one or more of the following features. For example, in some implementations, the biofuel cell device can further include an electrically conductive underlayer, e.g., formed of an electrically conductive material such as silver or copper, on the substrate and underneath the anode and cathode, respectively, e.g., in which the electrically conductive underlayer is structured as separated structures corresponding to the anode and cathode and electrically coupled to the load. In some implementations, the substrate of the biofuel cell device can be configured as an electrically insulative and flexible material. For example, the substrate can include a textile material. In some implementations, the biofuel cell device can further include a container on the substrate structured to contain the biological fluid in a region surrounding the anode and the cathode. In some implementations, the anode of the biofuel cell device can further include an electroactive mediator to facilitate electron transfer between an active site of the catalyst and the surface of the anode. In some implementations, the electrically conductive material of the anode can be configured of a carbon-based ink material. For example, the anode can be over-oxidized to form carbon-oxygen functional groups and edge-plane sites. In some implementations, the anode can further include carbon nanotubes, e.g., which can form the electrically conductive material of the anode and/or be configured on the surface of the anode. In some implementations, the anode can include a freely-diffusing electroactive redox mediator (e.g., attached to the surface of the anode) to interface an active site of the enzyme with the surface of the anode. In some implementations, the electrically conductive material of the cathode can be configured of a noble metal catalyst (e.g., such as platinum or palladium). In some implementations, the electrically conductive material of the cathode can be configured of a carbon-based ink material. For example, the carbon-based ink cathode can also include the noble metal catalyst as part of the cathode material. In some examples, the noble metal catalyst can be dispersed in the carbon-based ink material of the cathode. Also, in some examples, the noble metal catalyst can be configured on the surface of the cathode. For example, the cathode can be over-oxidized to form carbon-oxygen functional groups and edge-plane sites. In some implementations, the cathode can include carbon nanotubes, e.g., which can form the electrically conductive material of the cathode and/or be configured on the surface of the cathode. In some implementations, the cathode can further include an enzyme to facilitate the reduction of the oxygenated substance in the biological fluid to form the second product. For example, the enzyme can include, but is not limited to, laccase, bilirubin oxidase, tyrosinase, or polyphenol oxidase. In some implementations, the enzyme can be encased in a porous scaffold structure formed of the conducting polymer on the surface of the cathode, e.g., in which the conducting polymer includes, but is not limited to, polyaniline, polypyrrole, polythiophene, poly(3,4-ethylenedioxythiophene), poly(p-phenylene sulfide), polyfluorine, polyphenylene, polypyrene, polyazulene, polynaphthalene, poly(acetylene), poly(p-phenylene vinylene), or polyphenyldiamine. In some implementations, the enzyme can be entrapped in a permeable-selective membrane coupled to the surface of the cathode. In some implementations, the enzyme can be electrostatically bound to the surface of the cathode. In some implementations, the cathode can include a freely-diffusing electroactive redox mediator (e.g., attached to the surface of the cathode) to interface an active site of the enzyme with the surface of the cathode.

In another aspect, a biofuel cell device includes a substrate of an electrically insulative material, an anode formed on the substrate of an electrically conductive material, the anode including a catalyst to facilitate the conversion of a fuel substance in a biological fluid to a first product in an oxidative process that releases electrons captured at the anode, thereby extracting energy from the fuel substance, a cathode configured on the substrate adjacent to the anode and separated from the anode by a spacing region, the cathode formed of a material that is electrically conductive and including an electroactive mediator capable of reducing a non-oxygenated substance in the biological fluid to a second product in a chemical reduction process in which the second product gains electrons, and a load configured of one or more electrical circuit elements electrically coupled between the anode and the cathode via electrical interconnects to obtain the extracted energy as electrical energy.

In another aspect, a biofuel cell system includes a biofuel cell module and a power storage module. The biofuel cell module includes a container structured to include an opening on a top surface and a hollowed interior to contain a fluid (e.g., a biological fluid, such as urine, perspiration, saliva, among others) including a fuel substance (e.g., such as glucose, alcohol, lactic acid, urea, uric acid, ascorbic acid, among others); an array of biofuel cells formed on a flexible substrate and contained in the container, in which a biofuel cell of the array includes: an anode formed on the flexible substrate of an electrically conductive material, the anode including a catalyst to facilitate the conversion of the fuel substance to a first product in an oxidative process that releases electrons captured at the anode, thereby extracting energy from the fuel substance, a cathode positioned adjacent to the anode on the flexible substrate and separated from the anode by a spacing region, the cathode formed of a material that is electrically conductive and capable of reducing an oxygenated substance in the biological fluid to a second product in a chemical reduction process in which the second product gains electrons, and electrical interconnects connecting the anode and the cathode to an anode electrode contact pad and a cathode electrode contact pad, respectively; and a first electrical interface and a second electrical interface in electrical connection with the anode electrode contact pad and the cathode electrode contact pad, respectively. The power storage module includes a housing including a releasable attachment component to attach to and detach from the biofuel cell module, in which the attachment component seals the opening when attached; an electrical storage unit contained within the housing and configured of one or more electrical circuit elements electrically coupled to the first electrical interface and the second electrical interface when the attachment component is attached to the power storage module, in which the electrical storage unit is configured to store the extracted energy as electrical energy; and an electrical outlet configured on an outer surface of the power storage module and electrically coupled to the electrical storage unit, in which the electrical outlet is structured to electrically interface with a device to provide power to the device.

In another aspect, a method to fabricate a biofuel cell includes depositing an electrically conductive ink on a substrate to form an anode electrode and a cathode electrode adjacent to and separated from one another, the depositing including printing the ink on a stencil placed over the substrate, the stencil including a patterned region configured in a design of the anode and the cathode to allow transfer of the ink on the substrate, and the stencil inhibiting transfer of the ink in areas outside the patterned region; and the method includes curing the electrically conductive ink to produce a biofuel cell device.

Implementations of the fabrication method can optionally include one or more of the following features. For example, the curing can include at least one of applying heat or ultraviolet radiation to the deposited ink on the substrate. For example, the ink can be a carbon-based ink including noble metal nanoparticles dispersed in the ink, e.g., in which the carbon-based ink includes an enzymatic catalyst dispersed in the ink. For example, the substrate can be of an electrically insulative and flexible material, e.g., such as a textile material. In some implementations, the method can further include forming an electrically conductive layer under the anode electrode and cathode electrode by printing an ink of an electrically conductive material on a first stencil placed over the substrate, the first stencil including a printing region configured in a first design of conduit wires connecting to each of the anode and the cathode, the printing region allowing transfer of the ink on the substrate, and the first stencil inhibiting transfer of the ink in areas outside the printing region; and the method can further include curing the electrically conductive ink to produce a biofuel cell device. In some implementations, the method can further include: depositing an electrically insulative ink on the substrate to form an insulative layer that exposes the anode electrode and the cathode electrode, the depositing including printing the electrically insulative ink on a second stencil placed over the substrate, the second stencil including a printing region configured in a second design to allow transfer of the ink on the substrate, the second stencil inhibiting transfer of the ink in areas outside the printing region; and the method can further include curing the electrically insulative ink. In some implementations, the method can further include depositing carbon nanotubes to the surface of at least one of the anode electrode or the cathode electrode. In some implementations, the method can further include depositing an enzyme catalyst to the surface of at least one of the anode electrode or the cathode electrode, in which the depositing includes performing at least one of: encasing the enzyme catalyst in a porous scaffold structure formed of a conducting polymer on the surface of the electrode; covalently binding the enzyme catalyst to the surface of the electrode; entrapping the enzyme catalyst in a selectively permeable membrane coupled to the surface of the electrode; or electrostatically binding the enzyme catalyst to the surface of the electrode. In some implementations, the method can further include depositing an electroactive redox mediator to the surface of at least one of the anode electrode or the cathode electrode, in which the electroactive redox mediator facilitates the transfer of electrons between the electrode and the active site of the enzyme catalyst.

In another aspect, an epidermal biofuel cell device includes a substrate formed of a flexible electrically insulative material structured to adhere to the skin of a user, an anode formed on the substrate of an electrically conductive material, the anode including a catalyst to facilitate the conversion of a fuel substance in a biological fluid to a first product in an oxidative process that releases electrons captured at the anode, thereby extracting energy from the fuel substance, a cathode configured on the substrate adjacent to the anode and separated from the anode by a spacing region, the cathode formed of a material that is electrically conductive and capable of reducing an oxygenated substance in the biological fluid to a second product in a chemical reduction process in which the second product gains electrons, and an anode electrode interface component and a cathode electrode interface component formed on the substrate and electrically coupled to the anode and the cathode, respectively, via electrical interconnects, in which the extracted energy is addressable as electrical energy at the anode electrode interface component and the cathode electrode interface component.

In another aspect, a method to fabricate an epidermal biofuel cell device includes depositing an electrically conductive ink on an electrically insulative paper substrate to form an anode electrode and a cathode electrode adjacent to and separated from one another and conduit wires connecting to each of the anode and the cathode, the depositing including printing the ink on a first stencil placed over the paper substrate, the first stencil including a patterned region configured in a design of the anode, cathode, and conduit wires to allow transfer of the ink on the paper substrate, and the first stencil inhibiting transfer of the ink in areas outside the patterned region; curing the electrically conductive ink; depositing an electrically insulative ink on the paper substrate to form an insulative layer that exposes the anode electrode and the cathode electrode, the depositing including printing the electrically insulative ink on a second stencil placed over the paper substrate, the second stencil including a printing region configured in a second design to allow transfer of the ink on the paper substrate, the second stencil inhibiting transfer of the ink in areas outside the printing region; curing the electrically insulative ink; and depositing an adhesive layer on the insulative layer that exposes the anode electrode and the cathode electrode, the adhesive substrate formed of a flexible electrically insulative material structured to adhere to the skin of a user, in which the paper substrate includes an upper layer and a base paper layer, the upper layer including a release agent coated on the base paper layer and structured to peel off to remove the paper substrate.

The subject matter described in this patent document can be implemented in specific ways that provide one or more of the following features applicable to a variety of industries, e.g., including, but not limited to, biomedical, healthcare, fitness/athletics and energy industries. For example, implementation of the exemplary printed biofuel cells can lower the cost of healthcare and alleviate the burden on the healthcare provider. Exemplary devices can include biofuel cells that provide low-cost, paper-thin power sources that can sustain implantable/body-worn medical devices, such as bionic implants and bioelectronics. The disclosed technology includes fabrication methods to produce the robust, high-power output, and inexpensive biofuel cells capable of processing a wide variety of biofuels. For example, the disclosed biofuel cell devices are capable of energy extraction from various biofuels that can include glucose and alcohol (in whole blood), lactate (in perspiration), and uric acid and urea (in urine). Additionally, the disclosed biofuel cell devices can also be implemented as remote power systems that can significantly lower the costs involved with energy generation. For example, the remote power systems can be used to generate and/or co-generate power in decentralized locations, e.g., such as developing areas that lack access to conventional (refined) fuels. Additionally, the disclosed biofuel cell devices can also be implemented in wastewater treatment, implantable biomedical devices, fitness, and combat domains, e.g., due to its ability to process a wide array of widely-available fuels, thus serving as a core component of emerging renewable energy technologies.

The above and other aspects and implementations of the disclosed technology are described in greater detail in the drawings, the description and the claims.

BRIEF DESCRIPTION OF THE DRAWINGS

FIGS. 4A and 4B show schematics of an exemplary biofuel cell system for sustaining the power needs of a user in a remote environment.

FIG. 8A shows an image of an exemplary tattoo biofuel cell device attached to a human wrist.

FIG. 8B shows a data plot of polarization curves of a functionalized anode of an exemplary tattoo biofuel cell device.

FIG. 8C shows a data plot of the power density of an exemplary tattoo biofuel cell device.

Like reference symbols and designations in the various drawings indicate like elements.

DETAILED DESCRIPTION

Figure 1A:
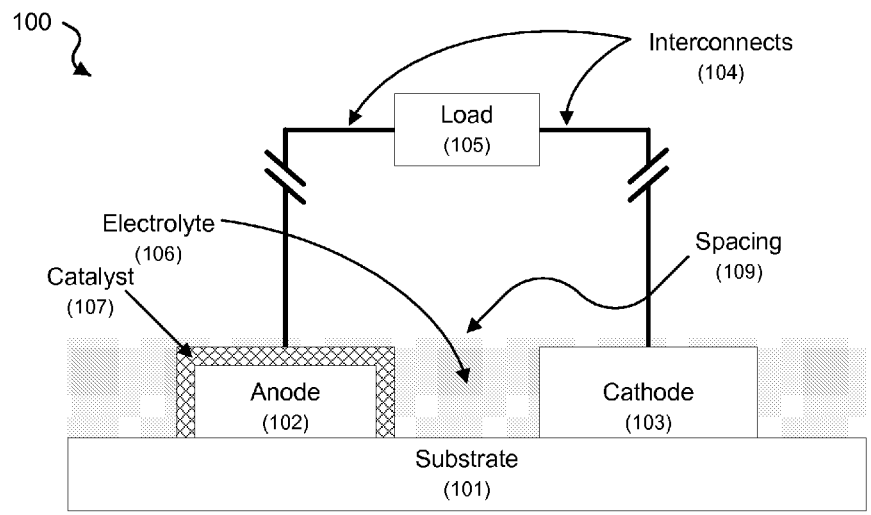
FIG. 1A shows a block diagram of an exemplary biofuel cell device.

Conventional fuel cell technologies generally include large solid-state devices that employ costly mechanical and chemical components. For example, some existing fuel cell devices can generate power from inorganic fuels, but many of these devices produce substantial carbon footprints when processed and refined. Also, due to the size and expense associated with existing fuel cell devices, there has not been a widespread commercial adoption since their introduction and the technology has been limited to particular applications, e.g., such as in the Space Shuttle program and automotive applications.

Biofuel cells are a class of fuel cell devices that employ enzymes or microbes as a bioprocessing contingent to derive power from various fuel substances such as organic, biochemical, and/or biological compounds which can be found in a variety of biological mediums. Biofuel cells can offer promise for the generation of energy from renewable fuel sources. Some existing devices to generate energy from renewable fuel sources have traditionally been plagued by poor power densities, limited lifetimes, and the inability to scale the technology to address any practical commercial needs, e.g., confining them to the research domain. Particular requirements need to be met to be practically applicable in a wide variety of applications, e.g., which can include high power density, power efficiency, long-term operation, miniaturization, low weight, and cost-parity with competing power generation systems, etc. For example, other field-deployable and mobile power technologies including batteries and photovoltaic devices can address several of these challenges, albeit they still cannot match the energy density (e.g., in the case of both batteries and photovoltaics), operational lifetime, or light weight (e.g., in the case of batteries) offered by biofuel cell devices. Also, batteries are merely energy storage devices rather than energy generation systems, and once the stored charge is depleted (e.g., which can be within several hours), the battery becomes a useless encumbrance. On the other hand, photovoltaics produce very little power (when used for mobile embodiments) and can only generate power during daylight hours, hence severely inhibiting their practical utility in field-deployable applications.

The disclosed technology includes devices, systems and methods of production of printed biofuel cells.

For example, the disclosed biofuel cells can enable the realization of conformal and paper-thin power sources that can provide continual power to portable electronic devices and implantable/body-worn biomedical devices. The disclosed technology includes biofuel cell devices capable of direct electron transfer from selected biocatalysts and high-throughput thick-film fabrication processes to produce the printed biofuel cells. The disclosed technology includes a biofuel cell architecture that can be used to derive useful amounts of power from unprocessed and renewable biological/organic fuel sources including, e.g., blood, urine, sweat, saliva, lacrimal fluid, sewage, and other wastewater sources. For example, the disclosed biofuel cell devices can be printed on lightweight plastic substrates rather than mechanically assembled using sophisticated, heavy, and expensive electrochemical components. The disclosed biofuel cell devices can include biocatalysts as part of the electrode heterostructure that obviate the need for precious metal catalysts, e.g., which can further reduce costs.

In one aspect of the disclosed technology, a biofuel cell device includes a substrate, an anode formed on the substrate of an electrically conductive material, the anode including a catalyst to facilitate the conversion of a fuel substance in a biological electrolytic fluid to a first product in an oxidative process that releases electrons captured at the anode, thereby extracting energy from the fuel substance, a cathode configured on the substrate adjacent to the anode and separated from the anode by a spacing region, the cathode formed of a material that is electrically conductive and capable of reducing an oxygenated substance in the biological fluid to a second product in a chemical reduction process in which the second product gains electrons, and a load (e.g., which can be configured as one or more electrical circuit elements) in electrical connection between the anode and the cathode via electrical interconnects to obtain the extracted energy as electrical energy. For example, the biological fluid can include, but is not limited to, perspiration, blood, urine, lacrimal fluid, or saliva. The fuel substance can include, but is not limited to, glucose, alcohol, lactic acid, urea, uric acid, or ascorbic acid. For example, the catalyst can include, but is not limited to, glucose oxidase, lactate oxidase, urate oxidase, or ascorbate oxidase. In some implementations of the biofuel cell device, the catalyst can be dispersed within the material forming the anode and/or coated as a layer on the surface of the anode. Additionally or alternatively, the catalyst can be entrapped within an electrically conductive polymeric structure formed by electropolymerization process on the surface of the anode. Additionally or alternatively, the catalyst can be covalently bound to the surface of the anode. Additionally or alternatively, the catalyst can be entrapped in a permeable-selective membrane coupled to the surface of the anode. Additionally or alternatively, the catalyst can be electrostatically bound to the surface of the anode.

FIG. 1A shows a block diagram of an exemplary biofuel cell device 100. The biofuel cell device 100 includes a substrate 101 of an electrically insulative material, which can be flexible or rigid. The biofuel cell device 100 includes an anode electrode 102 and a cathode electrode 103 on the substrate 101, in which the anode electrode 102 and the cathode electrode 103 are positioned adjacent to and separated from one another by a spacing region 109. The anode electrode 102 includes a catalyst 107, which can be configured to the anode in at least one of the following configurations: (i) the catalyst 107 dispersed within the anode material of the anode electrode 102; (ii) the catalyst 107 coated as a layer on the surface of the anode electrode 102; (iii) the catalyst 107 entrapped by an electropolymerized conducting polymer formed on the surface of the anode electrode 102; (iv) the catalyst 107 entrapped by a selectively permeable scaffold structure, e.g., such as Nafion or chitosan, formed on the surface of the anode electrode 102; (v) the catalyst 107 covalently bonded to the surface of the anode electrode 102; or (vi) the catalyst 107 electrostatically anchored to the surface of the anode electrode 102. The biofuel device 100 includes a load 105 electrically coupled to the anode and the cathode via electrical interconnects 104. The substrate 101 can facilitate an electrolytic fluid 106 containing a fuel substance on its surface that can immerse the spacing region 109 between the anode 102 and cathode 103. The electrolytic fluid 106 can include a biological fluid, e.g., such as perspiration, blood, urine, lacrimal fluid, or saliva, containing a biofuel, e.g., such as glucose, alcohol, lactic acid, urea, uric acid, or ascorbic acid. At least some of the components of the biofuel device 100, e.g., such as the cathode 103 and the anode 102, can be created using printing methods as described later in this patent document, e.g., which can include screen-printing, roll-to-roll printing, aerosol deposition, and inkjet printing techniques. In some implementations, the biofuel device 100 can include a proton-exchange membrane separator employed in the spacing region 109 to inhibit the conduction of electrons through the electrolytic medium. For example, the proton-exchange membrane separator can be printed on the substrate 101 in the spacing region 109.

Figure 1B:
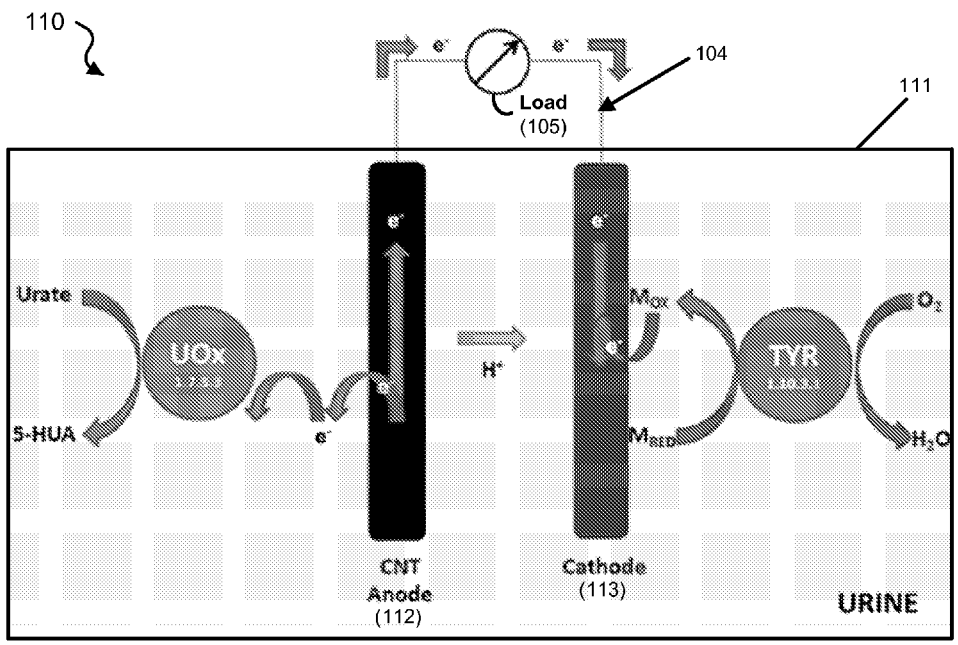
FIG. 1B shows a schematic illustration of an exemplary biofuel cell that includes a functionalized anode and cathode to extract electrical energy from biofuel in urine.

FIG. 1B shows a schematic illustration of a biofuel cell 110 that includes a catalyst/carbon nanotube-functionalized anode 112 positioned adjacent and separated from a functionalized cathode 113 on a substrate 111 to extract electrical energy from biofuel in urine. The functionalized anode 112 includes carbon nanotubes (CNTs) that can be configured, for example, on the surface of the anode or within the electrically conductive material of the anode, to further improve the electron transport functionality of the anode electrode. For example, CNTs can be functionalized on the surface of the anode to reduce the distance between the active site of the entrapped catalyst and the electrode, which can increase the effective catalytic surface area of the anode 112. In some implementations, the cathode 113 can also be functionalized to include CNTs to enhance electron transport of the cathode electrode. The functionalized anode 112 also includes an enzymatic catalyst, which is shown in FIG. 1B as urate oxidase (UOx). The enzymatic catalyst UOx can be entrapped to the functionalized anode 112 in any of the configurations (i)-(vi) described in FIG. 1A, e.g., which can prevent leeching of UOx into the urine and thereby maintaining efficiency of the biofuel cell 110 with respect to time. The cathode is the electrode at which reduction occurs, and the oxygen-containing substance can be reduced at the functionalized cathode 113 by a noble metal (e.g., such as platinum or palladium) or nickel formed within the cathode material and/or by an oxygen-reducing enzyme (e.g., such as laccase, bilirubin oxidase, tyrosinase, or polyphenol oxidase) coupled to the cathode. As shown in FIG. 1B, the functionalized cathode 113 is functionalized to include the enzyme tyrosinase (TYR). For example, tyrosinase can be entrapped in an oxygen-rich perfluorocarbon material coupled to the surface of the functionalized cathode 113 or in any of the configurations (i)-(vi) described in FIG. 1A.

In this example, the biofuel cell 110 is shown to be exposed to urine deposited over the active surface of the device. Urine includes the biofuel substance urate, also known as uric acid. The enzyme urate oxidase can catalyze the conversation of urate to 5-hydroxy uric acid (5-HUA) in an oxidation process that results in urate losing electrons, which are received at the UOx/CNT-functionalized anode 112. The TYR-functionalized cathode 113 can reduce an oxygenated substance, e.g., such as oxygen ($O_2$), present in the urine that results in the oxygenated substance gaining electrons in a reduction process. For example, if the medium is an aqueous medium, such as urine, the reduction will result in the formation of water, as protons ($H^+$) will flow across the solution, e.g., from the anode to the cathode. The biofuel cell 110 includes the load 105 via the interconnects 104, which can be externally interfaced to the electrodes on the substrate 111. The electrical connection of the load 105 between the UOx/CNT-functionalized anode 112 and the functionalized cathode 113 can facilitate an electrical current generated by the captured electrons from the catalytic conversion of urate to 5-HUA at the anode 112 when the cathode 113 is at a higher electrical potential. Electroactive mediators ($M_{OX}/M_{RED}$) can be attached to the functionalized cathode 113 to be deployed in the urine to electrochemically excite the active site of the enzyme TYR to enhance the reduction of the oxygen-containing substance from electrons that arrive at the cathode 113. Examples of the $M_{OX}/M_{RED}$ can include methylene blue (MB), methylene green (MG), tetrathiafulvalene (TTF), Prussian blue, and Meldola's blue.

Figure 1C:
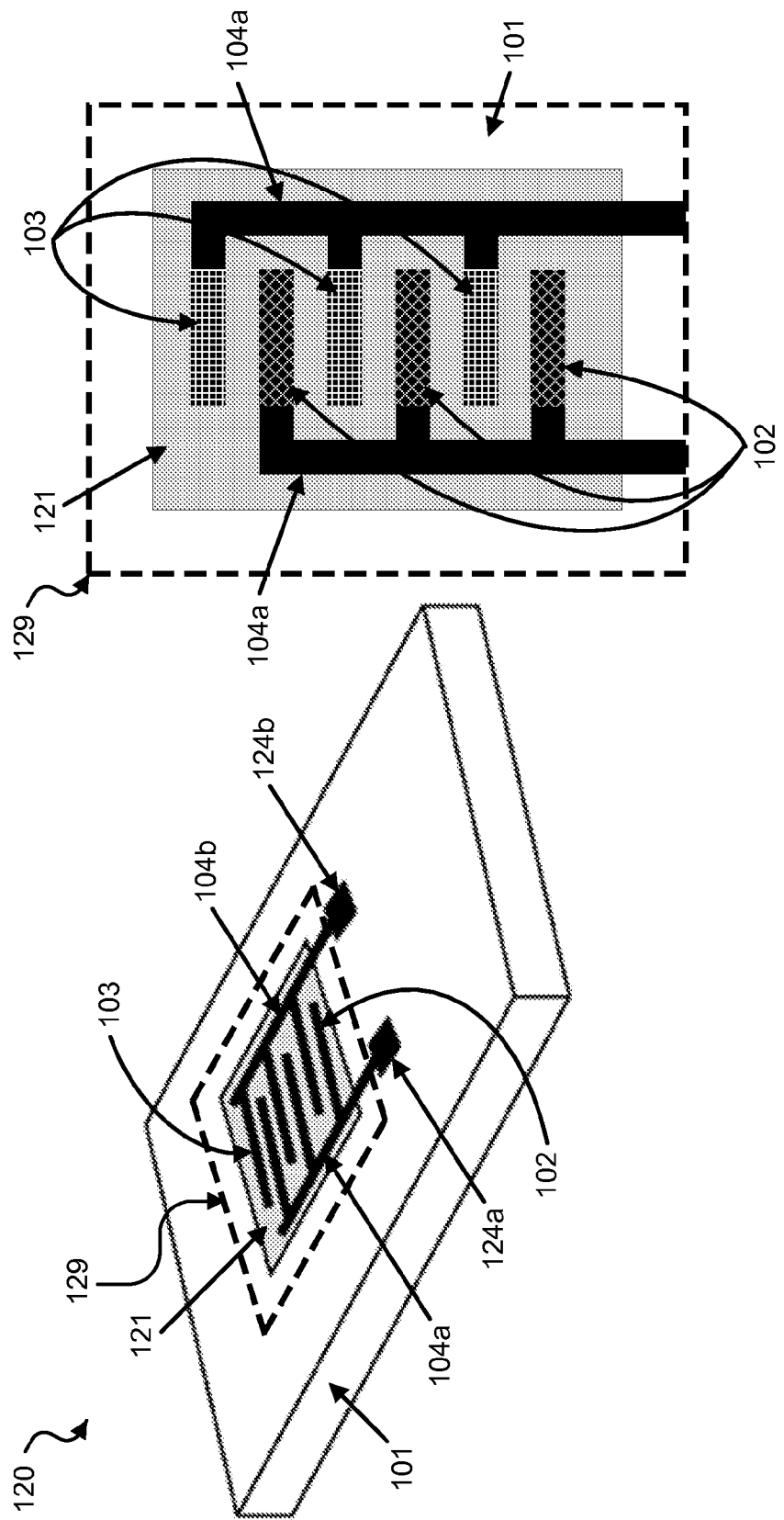
FIG. 1C shows a schematic of an exemplary biofuel cell strip device on a flexible substrate including an interdigitated array of anode and cathode electrodes.

FIG. 1C shows a schematic of an exemplary biofuel cell strip device 120 on a flexible substrate 101 that includes an interdigitated array of the anode electrodes 102 and the cathode electrodes 103 formed of a screen-printed carbon ink material embedded in a fluid reservoir 121 that contains a biological fluid having a fuel substance. The array of anode electrodes 102 are connected to a conduit 104a of an electrically conductive material configured on the substrate 101 that terminates at a contact pad 124a. The array of cathode electrodes 103 are connected to a conduit 104b of an electrically conductive material configured on the substrate 101 that terminates at a contact pad 124b. The biofuel cell strip device 120 includes a load, e.g. such as an electrical circuit element, externally interfaced to the interdigitated array of the anode and cathode electrodes via an electrical connection with the contact pads 124a and 124b. Alternatively, for example, in some implementations of the device 120, the load can be configured on the substrate 101 and electrically connected between the contact pads 124a and 124b. In some implementations, the biofuel cell device 120 can further include an electrically conductive underlayer, e.g., formed of an electrically conductive material such as silver or copper, on the substrate 101 and underneath the interdigitated array of the anode electrodes 102 and the cathode electrodes 103 and conduits 104a and 104b. In some implementations, the biofuel cell device 120 can further include a container on the substrate 101 structured to contain the biological fluid in a region surrounding the interdigitated array of the anode electrodes 102 and the cathode electrodes 103.

Figure 1D:
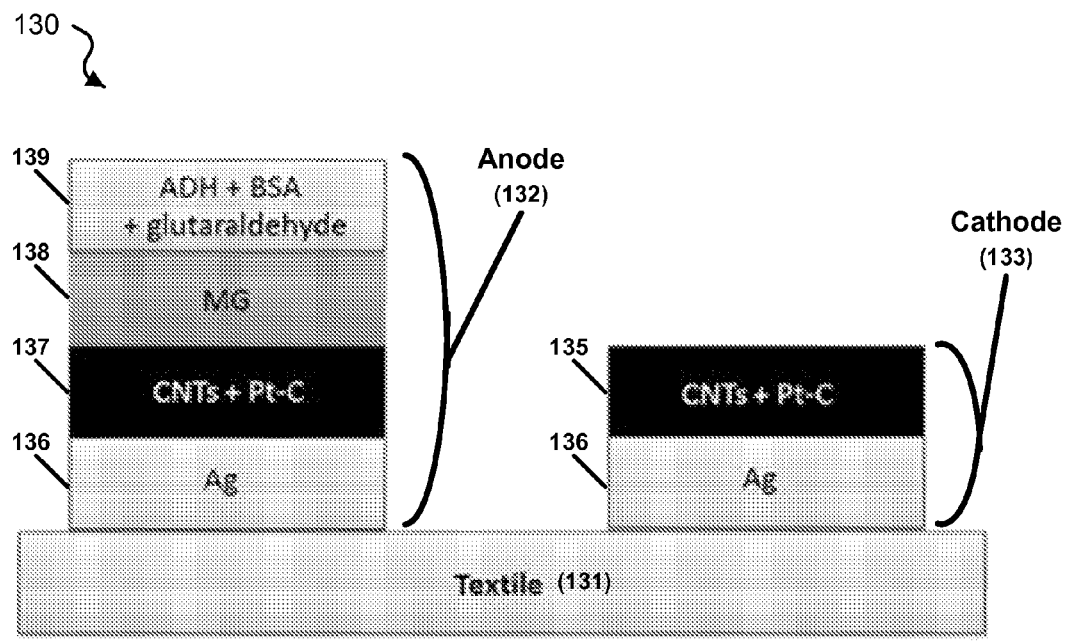
FIG. 1D shows a schematic of an exemplary biofuel cell on a textile substrate including a functionalized anode and cathode.

FIG. 1D shows a schematic of a biofuel cell 130 on a textile substrate 131 that includes a functionalized anode 132 positioned adjacent and separated from a functionalized cathode 133. The functionalized anode 132 is structured to include an electrically conductive underlayer 136 (e.g., such as silver) formed on the textile substrate 131 and configured under an anode material layer 137, e.g., which can be formed of a noble metal catalyst (e.g., such as Pt or Pd) and/or carbon ink material, in which CNTs are formed on the external surface of the anode material layer 137 and/or within the anode material layer 137, to further improve the electron transport functionality of the anode 132. The anode material layer 137 is capable of oxidizing a biofuel substance in a fluid in a oxidation process in which the biofuel loses electrons that are captured at the anode material layer 137. The functionalized anode 132 also includes an electroactive mediator layer 138 configured on the anode material layer 137. For example, the electroactive mediator layer 138 can include methylene green (MG). The electroactive mediator layer 138 can function to electrochemically excite the active site of an enzyme catalyst to enhance the oxidation of the biofuel to lose electrons that are received at the anode material layer 137. The functionalized anode 132 also includes an enzyme-functionalized layer 139 configured on the electroactive mediator layer 138 to serve as a catalyst to promote oxidation of the biofuel substance, thereby extracting electrons from the biofuel to the biofuel cell 130. In this example shown in FIG. 1D, the enzyme-functionalized layer 139 includes the bio-recognition element alcohol dehydrogenase (ADH) and the enzyme stabilizer bovine serum albumin (BSA), which are all substantially cross-linked with glutaraldehyde. The functionalized cathode 133 is structured to include the electrically conductive underlayer 136 formed on the textile substrate 131 and configured under a cathode material layer 135. The cathode material layer 135 is capable of reducing an oxygenated substance in the fluid in a chemical reduction process to gain electrons. For example, the cathode material layer 135 can be formed of a noble metal catalyst (e.g., such as Pt or Pd) and/or carbon ink material, in which CNTs are formed on the external surface of the cathode material layer 135 and/or within the cathode material layer 135, to further improve the electron transport functionality of the cathode 133.

Figure 1E:
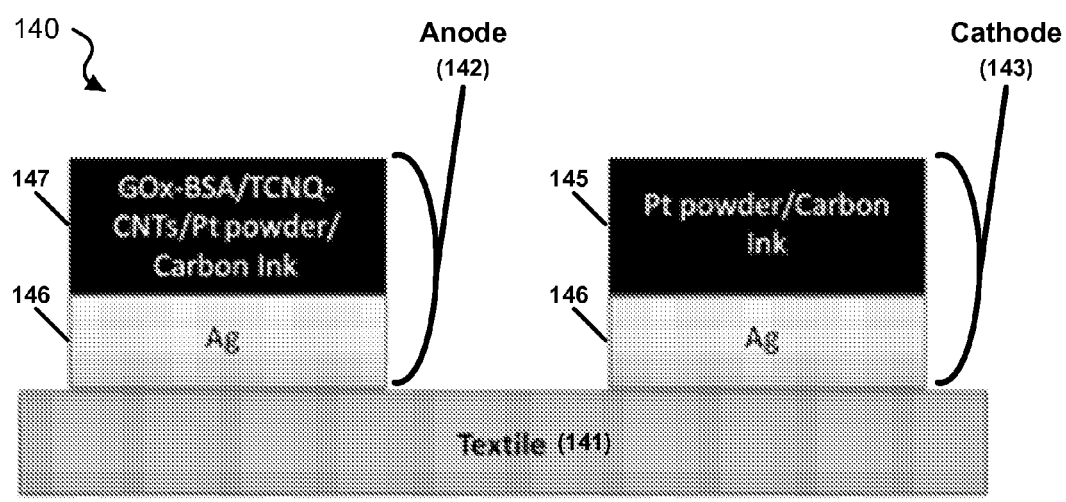
FIG. 1E shows a schematic of another exemplary biofuel cell on a textile substrate including a functionalized anode and cathode.

FIG. 1E shows a schematic of a biofuel cell 140 on a textile substrate 141 including a functionalized anode 142 positioned adjacent and separated from a functionalized cathode 143. The functionalized anode 142 is structured to include an electrically conductive underlayer 146 (e.g., such as silver) formed on the textile substrate 141 and configured under an anode material layer 147. The anode material layer 147 can be formed of a noble metal catalyst (e.g., such as Pt or Pd) configured as a fine-mesh powder dispersed within a carbon-based ink material, in which CNTs are formed on the external surface of the anode material layer 147 and/or within the anode material layer 147, to further improve the electron transport functionality of the anode 142. The anode material layer 147 can also include the bioprocessing element glucose oxidase (GOx) dispersed in the carbon-based ink material along with BSA and an electron acceptor substance tetracyanoquinodimethane (TCNQ). The anode material layer 147 is capable of oxidizing a biofuel substance in a fluid in a oxidation process in which the biofuel loses electrons that are captured at the anode material layer 147. The functionalized cathode 143 is structured to include the electrically conductive underlayer 146 formed on the textile substrate 141 and configured under a cathode material layer 145. The cathode material layer 145 is capable of reducing an oxygenated substance in the fluid in a chemical reduction process to gain electrons. For example, the cathode material layer 145 can also be formed of the noble metal catalyst (e.g., such as Pt or Pd) configured as a fine-mesh powder dispersed within the carbon-based ink material, in which CNTs are formed on the external surface of the cathode material layer 145 and/or within the cathode material layer 145, to further improve the electron transport functionality of the cathode 143.

Figure 1F:
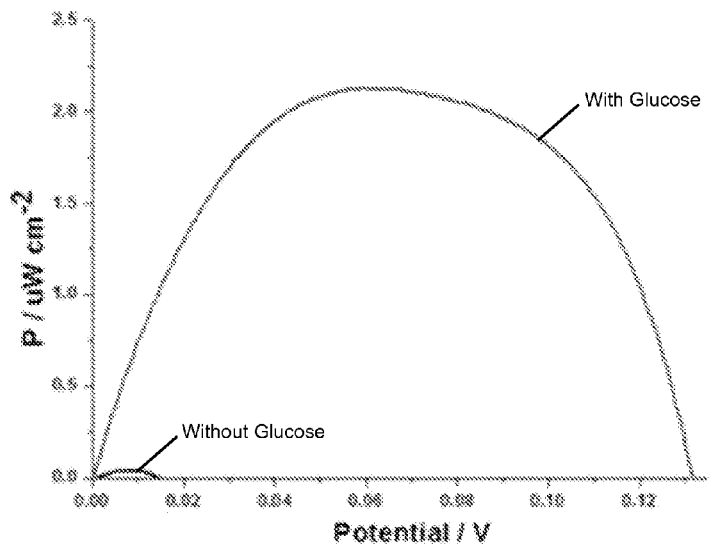
FIG. 1F shows a data plot of an exemplary power curve generated by an exemplary biofuel cell device in the presence and absence of a biofuel.

FIG. 1F shows a data plot of an exemplary power curve generated by an exemplary biofuel cell device in the absence of the biofuel glucose ('without glucose', black curve) and presence of the biofuel glucose ('with glucose', red curve). The data demonstrates the electrocatalytic ability of the exemplary biofuel cell to extract energy from the biofuel.

Figure 1G:
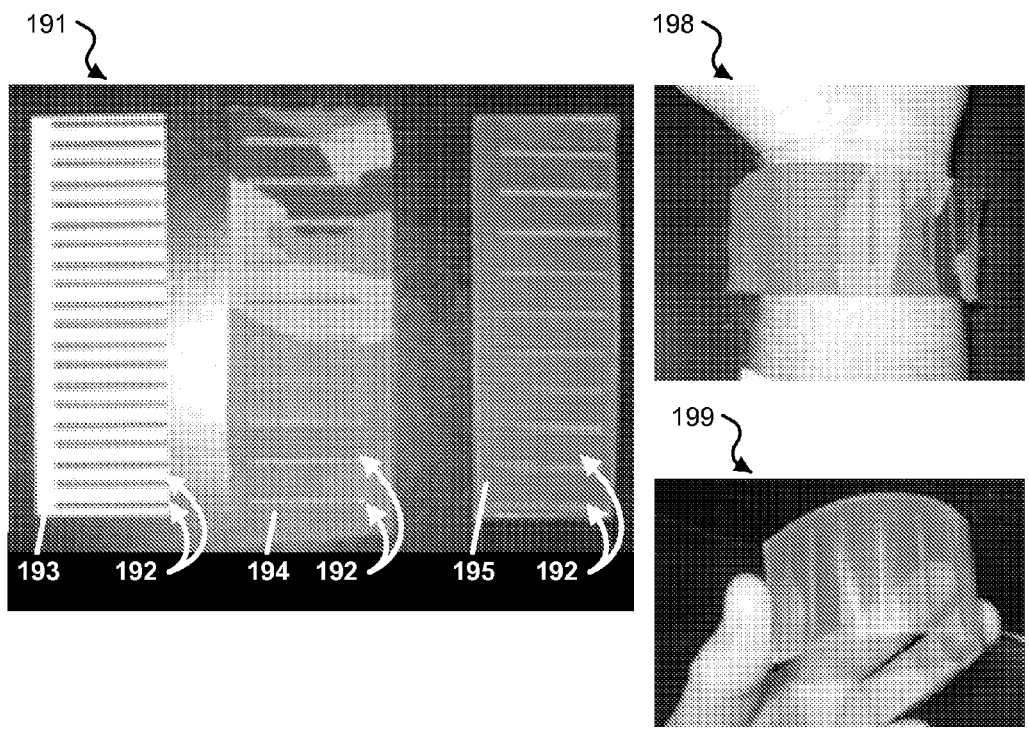
FIG. 1G shows images of exemplary printed biofuel cells fabricated using screen-printing techniques on various substrate materials.

FIG. 1G shows images of exemplary printed biofuel cells fabricated using screen-printing techniques on various substrate materials. FIG. 1G includes an image 191 showing the exemplary biofuel cell electrodes 192 printed on a ceramic substrate 193, a textile substrate 194, and a flexible plastic substrate 195 such as mylar. FIG. 1G includes an image 198 showing an exemplary biofuel cell printed on a textile. FIG. 1G includes an image 199 showing an exemplary biofuel cell printed on mylar.

In another aspect, the disclosed technology includes methods to fabricate the exemplary biofuel cell devices that include printing techniques and chemical functionalization of electrically conductive inks on a wide variety of rigid and flexible substrates for power generation. For example, the fabrication techniques can utilize high-throughput and low cost screen-printing, roll-to-roll processing, aerosol deposition, and inkjet techniques to produce printed biofuel cells. For example, an exemplary method of the disclosed technology involves the printing of specialized inks to form the anode and the cathode on the substrate, with the anode containing a catalyst (e.g., such as an enzyme or other protein) to catalyze the conversion of an organic/biological fuel substance in an electrolyte to a product in an oxidative process, thereby releasing electrons and generating an electrical current that can be employed to drive the load (e.g., of one or more electrical circuit elements), and with the cathode receiving electrons to reduce a reductant substance. In some implementations, the exemplary method can include functionalizing the cathode to include an enzyme (or other protein) catalyst. For example, the electrolyte can be an unprocessed biological/organic matrix (e.g., as blood, perspiration, lacrimal fluid, saliva, or urine) to mitigate the transport of protons from the anode to the cathode. The exemplary method can include printing the anode and cathode on any rigid substrate, e.g., such as a solid-state material, or any flexible substrate, e.g., including alumina, paper, mylar, polyethylene terephthalate (PET), Teflon (polytetrafluoroethylene (PTFE)), and various textiles/fabrics, among others. For example, the flexible substrates can be preconditioned through repeated mechanical deformation operations (e.g., flexing, bending, stretching, etc.) to give rise to micro-cracks in the anode and cathode morphology. These microcracks can increase the electrode surface area, thereby yielding greater power output. Moreover, the fabrication methodology can be scaled to create large electrode arrays and parallel stacks of fuel cells, thereby increasing the amount of power generated.

Figure 2:
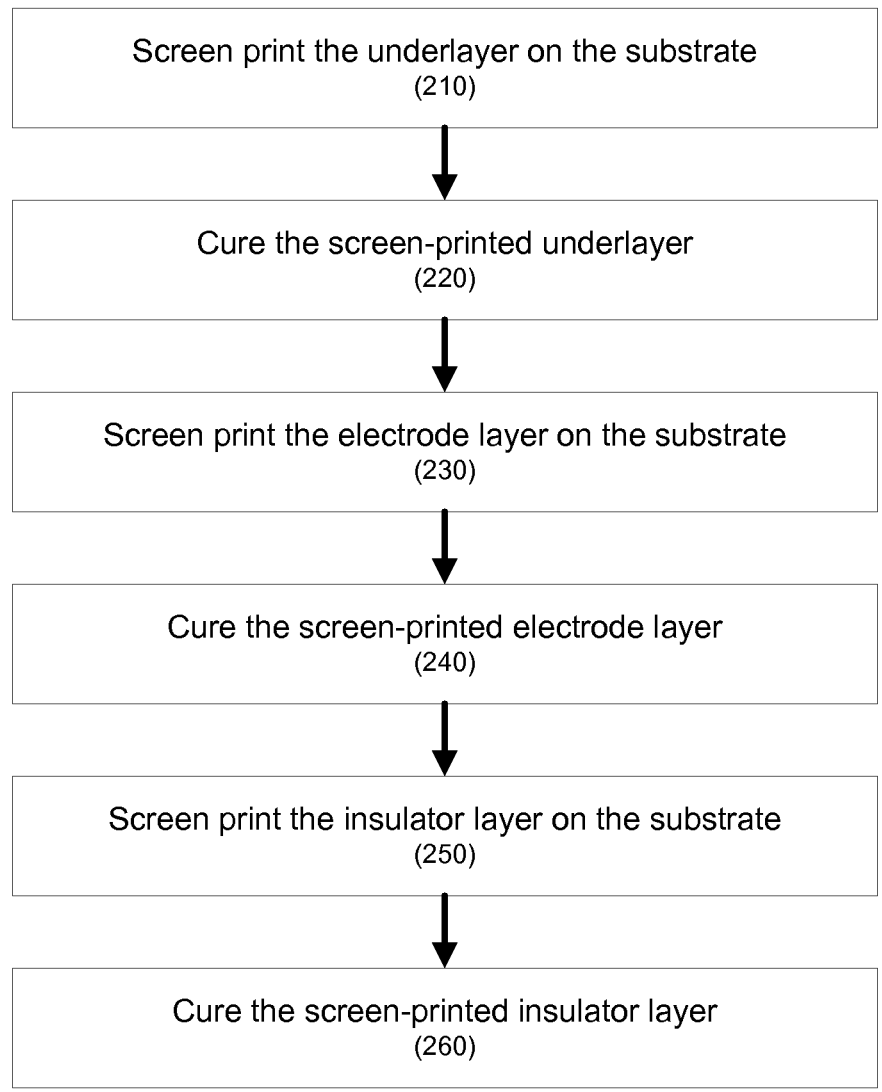
FIG. 2 shows a block diagram of a method to fabricate a printed biofuel cell.

FIG. 2 shows a block diagram of a method to fabricate a printed biofuel cell. The method includes a process 210 to screen print a layer of an electrically conductive material, e.g., such as the carbon-based conductive ink, on an electrically insulative substrate material. For example, the screen printing of the layer can include using a woven mesh screen to support an ink-blocking stencil or a through-hole stencil for the same use. The stencil can be formed in any desired shape or design to form the layer, which can include forming the electrical underlayer for the anode and cathode electrodes, the interconnects, and/or contact pads of a biofuel cell device. Likewise, an active layer defining the anode and cathode contingents as well as an insulative layer that defines the working biofuel cell geometry and prevents the conductive underlayer from a short-circuit may be implemented. The attached stencil forms open areas of mesh screen/stencil that transfer the carbon-based ink or other printable electrically conductive materials which can be extruded through the mesh screen/stencil as a sharp-edged image onto the substrate material, e.g., which can be rigid or flexible. In some implementations of the screen printing process 210, a fill blade or squeegee is moved across the screen stencil, forcing or pumping the ink material into the mesh openings for direct transfer during the squeegee stroke. The method includes a process 220 to cure the screen printed layer on the substrate, e.g., by thermally curing or UV curing techniques.

The method includes a process 230 to screen print an electrode layer of an electrically conductive material to form the anode and the cathode contingents on the substrate. For example, the screen printing of the electrode layer can include using a woven mesh to support a ink-blocking stencil, e.g., which can be configured in a desired shape or design to form the anode and cathode electrodes, to transfer the carbon-based ink or other printable electrically conductive materials to print the electrodes onto the screen printed underlayer. In some implementations, the method can begin with the process 230 to screen print the electrode layer directly onto the substrate material and forgo the processes 210 and 220. For example, the process 230 can be implemented to produce the anode and cathode electrodes in a single printing step. The method includes a process 240 to cure the screen printed electrode layer on the substrate, e.g., by thermally curing or UV curing techniques. In some implementations, the ink or other material used to screen print the electrode layer in the process 230 can include the catalyst material dispersed within the ink or other electrically conductive material. In some implementations, the process 230 can include using multiple stencils to screen print the anode and cathode electrodes separately or to form multiple layers of an anode and/or a cathode electrode heterostructure.

The method includes a process 250 to screen print an insulator layer of an electrically insulative material over the interconnects structures of the underlayer on the substrate. For example, the screen printing of the insulator layer can include using a woven mesh to support an electrically insulative material-blocking stencil, e.g., in which the stencil can be configured in a desired shape or design to form a region covering interconnects and other structures while exposing the anode and cathode electrodes. The method includes a process 260 to cure the screen printed insulator layer on the substrate, e.g., by thermally curing or UV curing techniques. In some implementations, the method can conclude with the process 240 to cure the electrode layer directly onto the substrate material and forgo the processes 250 and 260. Also, it is understood that the method can be implemented using roll-to-roll printing or processing, aerosol deposition, or inkjet printing techniques in the processes 210, 230, and/or 250.

For example, the components of the exemplary biofuel cell (e.g., including the anode and the cathode) can be printed using a specially-formulated ink composition. For example, porous carbon (PC) can be used to immobilize nanoparticles, e.g., such as platinum nanoparticles (PtNPs), to form carbon-based ink electrodes with increased surface area that facilitate high current densities and efficient mass transport of diffusional redox species. This exemplary metallized PC couples the attractive features of porous carbon with efficient electrocatalyic ability of three-dimensionally dispersed metal particles. For example, the metallized PC electrodes contain engineered micron-scale structures spanning seven orders of magnitude with defect-free highly controllable 3-D lattices and periodicity uniformly, e.g., which has been shown in samples in excess of 2 cm a side. In some implementations, an electrically conductive underlayer (e.g., such as silver or copper) can be printed on the substrate and cured at a suitable temperature. The electrically conductive underlayer can be printed to form separated structures corresponding to the placement of the anode and cathode. Subsequently, the cathode material is printed on the conductive underlayer structure(s) corresponding to the cathode. For example, the cathode material can include a metallic catalyst material such as a noble metal dispersed within the conductive carbon-based ink. The anode material is printed on the conductive underlayer structure(s) corresponding to the anode. For example, the anode material can include an electrically conductive material such as the carbon-based ink in which the enzyme catalyst is configured within the anode material or on the surface of the anode material.

In some implementations, the enzyme catalyst can either be embedded in the ink itself or electropolymerized in a second processing step using any one of a number of conducting polymers, e.g., such as polyaniline, polypyrrole, polythiophene, poly(3,4-ethylenedioxythiophene), poly(p-phenylene sulfide), polyfluorine, polyphenylene, polypyrene, polyazulene, polynaphthalene, poly(acetylene), poly (p-phenylene vinylene, and polyphenyldiamine, among others. For example, to encase the enzyme catalyst in the conducting polymer using electropolymerization, the method can include the application of a suitable deposition potential on the appropriate electrode while the device is immersed in a solution of the selected monomer. For example, the enzyme catalyst can be entrapped in a matrix of the conducting polymer. The conducting polymer entrapment can offer the ability to achieve a highly mesoporous network in which the biocatalyst may be immobilized while substantially increasing the effective active area of the electrode surface, e.g., thus giving rise to increased current densities. The conducting polymer can be synthesized upon the application of a suitable oxidation potential to the printed electrode, causing the monomer to electropolymerize onto the cathode surface from a base solution. A charged dopant can be implemented in the base solution to impart conductivity. For example, in order to properly immobilize and achieve fine dispersion of the enzyme within the conducting polymer matrix, a co-electrochemical deposition process can be implemented whereby the conducting polymer host can uptake the enzyme during the electropolymerization routine. For example, this can result in the uptake and dispersion of the enzyme in the polymer matrix from the base solution. For example, multi-walled CNTs can be employed at this step to provide a cross-linked network of conductive pathways to further facilitate electron transfer. For example, nickel or noble metal nanoparticles may also be added to the matrix to impart greater electrocatalytic surface area.

In other implementations, the enzyme catalyst can also be immobilized on the anode and/or the cathode electrode surface via other mechanisms, including covalent binding, electrostatic entrapment, or entrapment in a permeable-selective membrane, e.g., such as Nafion or chitosan. For example, the anode and/or cathode electrode can be structured to include a material having an opposite charge than that of the catalyst, e.g., which can be attached to the surface of the electrode, to electrostatically bind the catalyst to the anode and/or cathode. For example, the enzyme catalyst can be deposited on the surface of the anode and/or cathode and a selectively permeable membrane can be subsequently disposed over the enzyme catalyst-deposited electrode surface to entrap the catalyst in the membrane to the electrode.

The disclosed fabrication techniques include the ability to effectively immobilize the enzyme catalyst for extended durations while still maintaining its catalytic activity. For example, a biofuel cell device can be fabricated to include a nano-structured anode heterostructure capable of oxidizing a biofuel in a fluid medium (e.g., such as glucose in a blood). The exemplary fabrication technique can include the immobilization of the enzyme catalyst (e.g., such as glucose oxidase) on the anode electrode surface. In one example, in order to facilitate electron transfer for optimal power generation, the covalent binding of the biocatalytic layer to the electrode surface can be implemented. For example, more specifically, this can entail the chemical treatment of multi-walled carbon nanotubes to express abundant carboxyl (COOH) groups along its surface. Subsequently, the COOH-functionalized nanotubes may then be immersed in a specific molar-ratio mixture of 1-ethyl-3-(3-dimethylaminopropyl) carbodiimide (EDAC) and N-hydroxysuccinimide (NHS) to couple the enzyme catalyst (e.g., glucose oxidase) to the nanotube via direct amine binding, e.g., thus forming a strong, covalent tether and conducting backbone used to transport the electron from the active site of the enzyme to the electrode (and hence to the load). The enzyme catalyst is immobilized and remains tethered to the electrode surface, hence providing for augmented power density, e.g., in comparison with conventional drop-casting, cross-linking, or polymer entrapment techniques. Alternatively, in another example, a perm-selective membrane can be cast on the anode electrode surface to entrap the enzyme catalyst while permitting the fuel to diffuse through the matrix. Alternatively, in another example, the enzyme catalyst can be entrapped in a conducting polymer matrix in order to augment the surface area of the electrode and facilitate biocatalytic conversion of a biochemical substrate. Alternatively, in another example, the enzyme catalyst can be electrostatically bound to the electrode surface using an oppositely-charged interfacial agent, such as polyethyleneimine. Alternatively, in another example, the active site of the enzyme catalyst can be interfaced with the electrode using a freely-diffusing electrochemical redox mediator, e.g., such as MG, MB, TTF, etc.

In some implementations, the cathode can further include the noble metal catalyst electrodeposited on the unmodified electrode surface. For example, to electrodeposit the noble metal catalyst on the cathode surface, the method can further include a process to immerse the printed biofuel cell in a solution of the selected noble metal and apply a suitable deposition potential on the cathode electrode while the device is immersed.

In some implementations, the cathode can further include an enzymatic catalyst to facilitate a reduction process by which an oxygenated substance gains electrons to form a product. The method can include a process to add an enzyme catalyst on the cathode. For example, the enzyme catalyst can include, but is not limited to, laccase, bilirubin oxidase, tyrosinase, or polyphenol oxidase. In some examples, the method can include depositing the exemplary enzymatic catalyst and/or noble metal catalyst subsequent to fabricating the anode and cathode on the substrate, and as such, both the anode and cathode can be printed during the same printing step of the method. In some implementations, the method can include a process to print a proton-exchange membrane separator employed in the spacing region 109 that can function to inhibit the conduction of electrons through the electrolytic medium during operation of an exemplary biofuel cell of the disclosed technology.

Figure 3A:
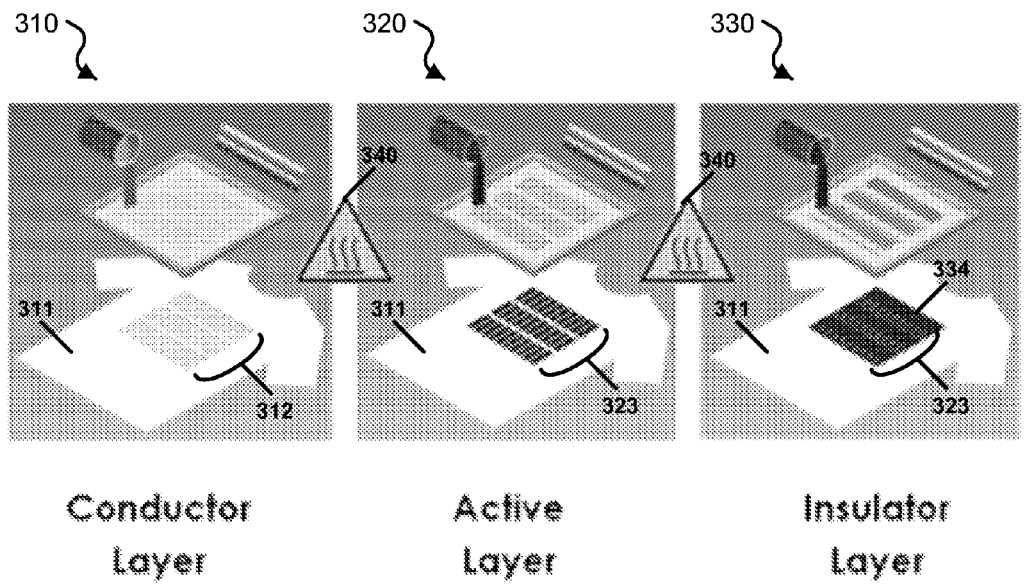
FIGS. 3A and 3B show exemplary illustrative diagrams of screen printing processes to fabricate biofuel cell devices.

FIG. 3A shows an illustrative diagram of a screen printing process showing three stages involved in the development of screen-printed electrodes (e.g., anodes and cathodes) in the fabrication of biofuel cell devices. In one example, the fabrication process includes a stage 310 to pattern a conductive underlayer 312 (e.g., silver) on a textile substrate 311. The fabrication process includes a stage 320 to pattern an active layer 323 including the cathode contingent (e.g., such as nickel, for catalytic reduction of hydrogen peroxide) and the anode contingent (e.g., such as a conductive carbon-based ink material, which can contain relevant COOH-modified CNT engineered nanomaterials dispersed in the ink for covalent enzyme immobilization). The fabrication process includes a stage 330 to pattern an insulative top layer 334 that exposes the active layer 323 to define the active area (cathode and anode electrodes) of the printed biofuel cell device. After each of the stages 310, 320, and 330, the substrate 311 is cured, as shown by the symbol 340 in FIG. 3A. The curing process can be implemented in a convection oven following each patterning stage.

Figure 3B:
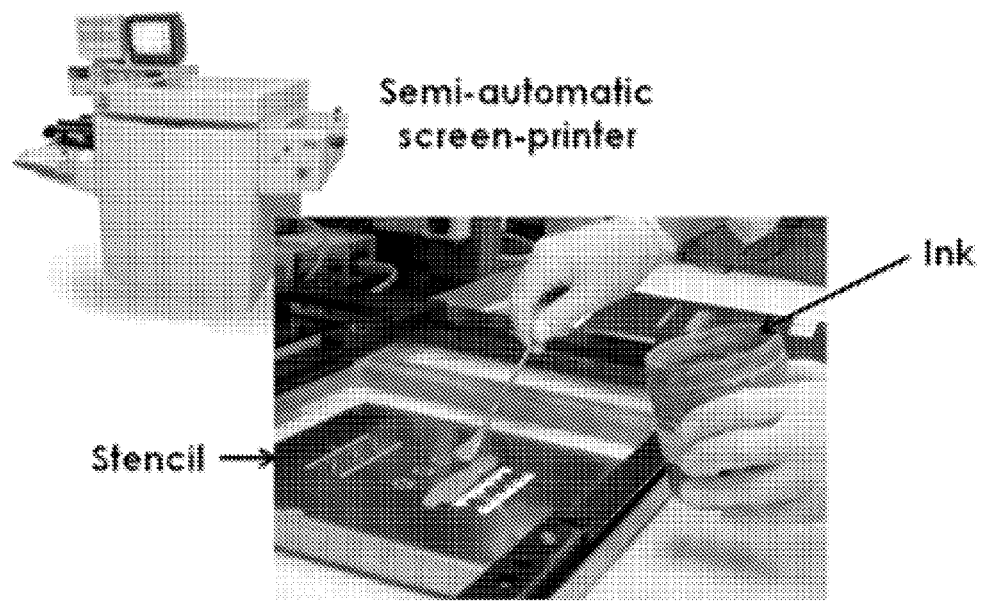

FIG. 3B shows an example of a semi-automatic screen printer that can be employed to pattern the electrodes on a substrate (e.g., such as the textile substrate 311) through a custom-fabricated stainless steel stencil, which is shown in the inset image. The exemplary stencil can be employed to pattern an array of electrodes for the biofuel cell device. For example, the disclosed technology can achieve a value-driven combination of high-throughput fabrication (e.g., greater than 10,000 individual biofuel cell elements produced per hour) and extremely low cost (e.g., such as for ~$20 of ink materials and other supplies). In some examples, such devices can be utilized for the detection of security threats on fabrics.

Figure 3C:
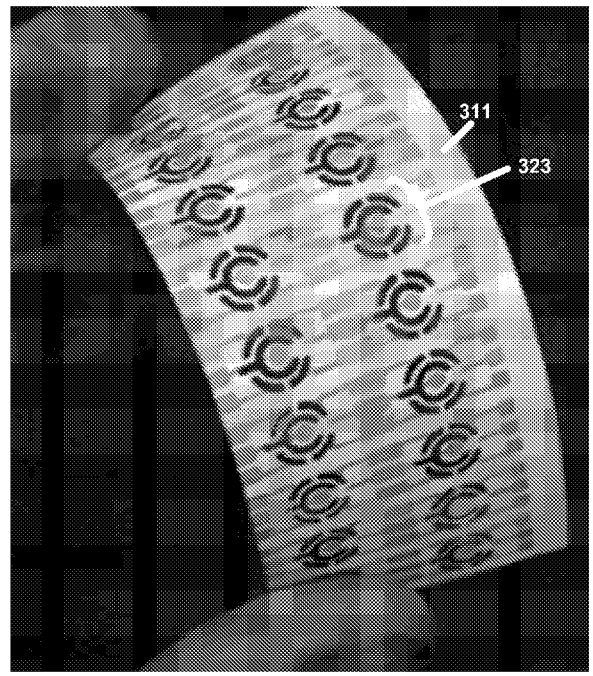
FIGS. 3C-3E show images of various configurations of exemplary printed biofuel cells.
Figure 3D:
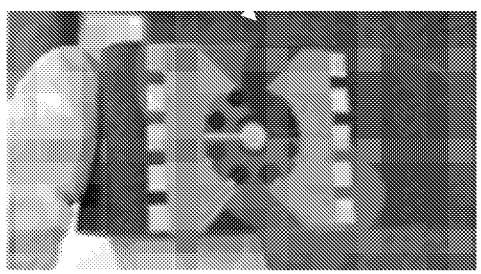
Figure 3E:
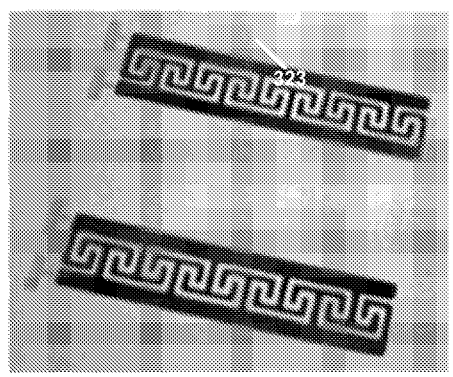

FIGS. 3C-3E show images of various configurations of exemplary printed biofuel cells. FIG. 3C shows an image of a stack of biofuel cell elements (e.g., the active layer 323 of anode and cathode contingents) fabricated on a flexible substrate (e.g., the substrate 311) using the described screen-printing fabrication techniques. Implementations of these exemplary biofuel cells can include providing power sources capable of sustaining remote sensors, fitness gear, and implanted medical devices in a cost-effective and non-invasive manner. FIG. 3D shows an image of exemplary biofuel cells printed on a textile substrate for perspiration-based power generation. FIG. 3E shows an image of exemplary biofuel cells printed on paper, e.g., which can be implemented as a low cost, one-time-use disposable device.

In some embodiments of the disclosed technology, the exemplary printed biofuel cells can be implemented in a biofuel cell system. In one exemplary embodiment, a biofuel cell system includes a biofuel cell module and a power storage module. The biofuel cell module can include a container structured to include an opening on a top surface and a hollowed interior to contain a fluid (e.g., a biological fluid, such as urine, perspiration, saliva, among others) including a fuel substance (e.g., such as glucose, alcohol, lactic acid, urea, uric acid, ascorbic acid, among others). The biofuel cell module can include an array of biofuel cells formed on a flexible substrate and contained in the container, in which a biofuel cell of the array includes: an anode formed on the flexible substrate of an electrically conductive material, the anode including a catalyst to facilitate the conversion of the fuel substance to a first product in an oxidative process that releases electrons captured at the anode, thereby extracting energy from the fuel substance; a cathode positioned adjacent to the anode on the flexible substrate and separated from the anode by a spacing region, the cathode formed of a material that is electrically conductive and capable of reducing an oxygenated substance in the biological fluid to a second product in a chemical reduction process in which the second product gains electrons; and electrical interconnects connecting the anode and the cathode to an anode electrode contact pad and a cathode electrode contact pad, respectively. The biofuel cell module can include a first electrical interface and a second electrical interface in electrical connection with the anode electrode contact pad and the cathode electrode contact pad, respectively. The power storage module can include a housing including a releasable attachment component to attach to and detach from the biofuel cell module, in which the attachment component seals the opening when attached. The power storage module can include an electrical storage unit contained within the housing and configured of one or more electrical circuit elements electrically coupled to the first electrical interface and the second electrical interface when the attachment component is attached to the power storage module, in which the electrical storage unit is configured to store the extracted energy as electrical energy. The power storage module can include an electrical outlet configured on an outer surface of the power storage module and electrically coupled to the electrical storage unit, in which the electrical outlet is structured to electrically interface with a device to provide power to the device.

FIGS. 4A and 4B show schematics of an exemplary biofuel cell system for sustaining the power needs of a user in a remote environment. FIG. 4A shows an exploded view of the exemplary biofuel cell system. The exemplary biofuel cell system includes an external module 401 that houses a container or cartridge 402. The module 401 is configured in a cylindrical geometry, but can also be configured in any shape. The cartridge 402 includes a hollowed interior that can contain printed biofuel cell devices 403 of the disclosed technology and a fluid medium including a biofuel substance that can contact the active sites of the printed biofuel cell devices 403 within the cartridge 402. For example, the printed biofuel cell devices 403 can utilize urine or wastewater as a source of fuel, such that the user of the exemplary biofuel cell system can power their other devices in remote regions, e.g., where traditional sources of fuel are not available. For example, the biofuel cells can be configured in a rolled biofuel cell (BFC) configuration that facilitates an array or multiple biofuel cells on a substrate capable of being rolled-up, e.g., to maximize the number of biofuel cells on the substrate. The rolled BFC 403 can include electrode contacts 405 that can be electrically connected to a load located in another section of the exemplary biofuel cell system. The exemplary biofuel cell system includes a cap with a voltage regulator 404 that can be attached to the module and electrically interfaced with the rolled BFC 403 (e.g., via the electrode contacts 405). In some implementations, the cap with a voltage regulator 404 can include a processing unit including at least a processor and a memory unit. In some implementations, the cap with a voltage regulator 404 can include an AC outlet 411 to provide AC electricity to other AC-operated devices and a DC outlet 412 to provide DC electricity to other DC-operated devices, as shown in FIG. 4B. In some implementations, the cap with a voltage regulator 404 can include a display 413 (e.g., such as an LCD display) and buttons 414 or other structures for a user interface with the processing unit of the exemplary biofuel cell system. For example, the display can provide the amount of power available in the exemplary biofuel cell system.

The described biofuel cell devices, systems, and fabrication processes can present many advantages and distinguishing features. For example, there is no requirement to modify the cathode with an enzyme (e.g., such as laccase or billirubin oxidase). Rather, one can use screen-printed ink functionalized with noble metal catalyst nanoparticles or simply electroplate the cathode with the noble metal (e.g., such as palladium or platinum). This can entail that the cathode is not limited by the catalytic ability of an enzyme, which can be substantially less prolific than inorganic catalysts. Also, for example, the anode and cathode can be printed side-by-side rather than on top of one another since an interstitial separator is not required between the anode and cathode. This can substantially reduce the number of processing steps and expense associated with fabrication and materials. More specifically, for example, the anode and cathode active geometry can be patterned in a single processing step. In another example, a greater variety of fuels using other enzymes can be processed. For example, one can process lactic acid (such as found in the blood or perspiration) through the incorporation of lactate oxidase in the anode. Similarly, uric acid (such as found in the urine) can be employed as a fuel via urate oxidase. In another example using the exemplary biofuel cell device, one can entrap the enzyme on the anode using conducting polymers, which provide a porous, conducting scaffold to immobilize the enzyme used and shuttle the electrons it yields to the anode. This exemplary technique can substantially increase the functional surface area of the electrode (e.g., greater catalytic area, hence providing greater power output) as well as provides a facile means for electron transport.

Some examples to further improve power input and efficiency of the disclosed biofuel cell devices can include the following. One exemplary technique to improve power input and efficiency can include using interdigitated electrodes that can achieve high active surface area. Another exemplary technique to improve power input and efficiency can include placing the anode and cathode in close proximity to facilitate efficient $H^+$ transfer, e.g., due to minimized diffusion length. Another exemplary technique to improve power input and efficiency can include modifying electrodes with nanomaterials (e.g., nanoparticle catalysts, carbon nanotubes (CNTs), etc.) to achieve direct electron transfer from enzyme's active site to the electrode, e.g., rather than using a mediator.

Figure 5A:
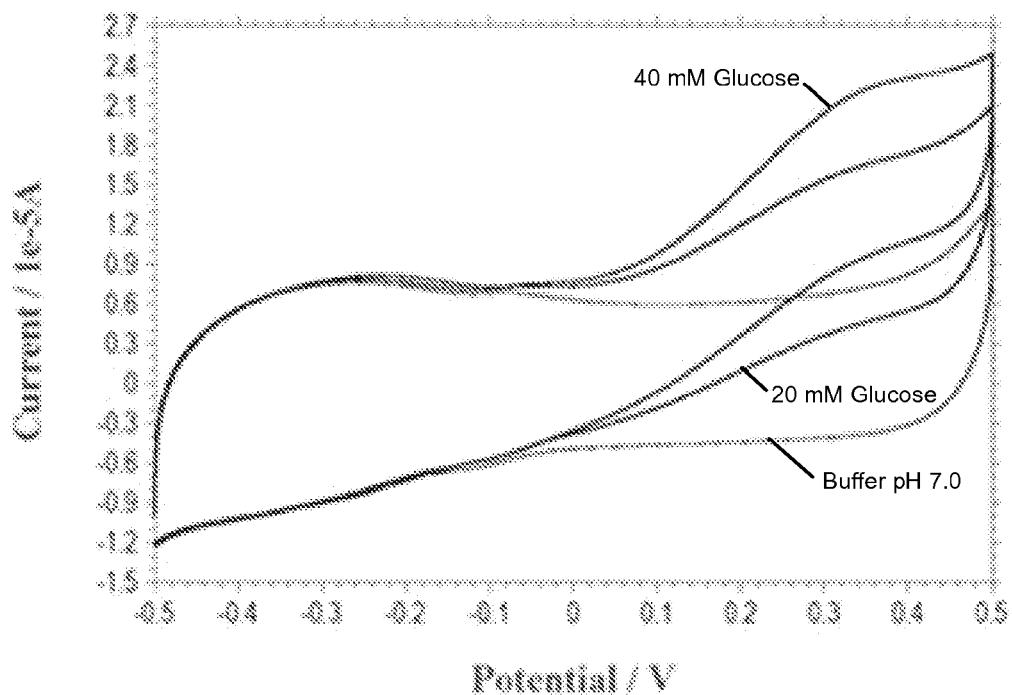
FIGS. 5A-5C show I-V data plots demonstrating the catalytic ability of exemplary biofuel cell devices.
Figure 5B:
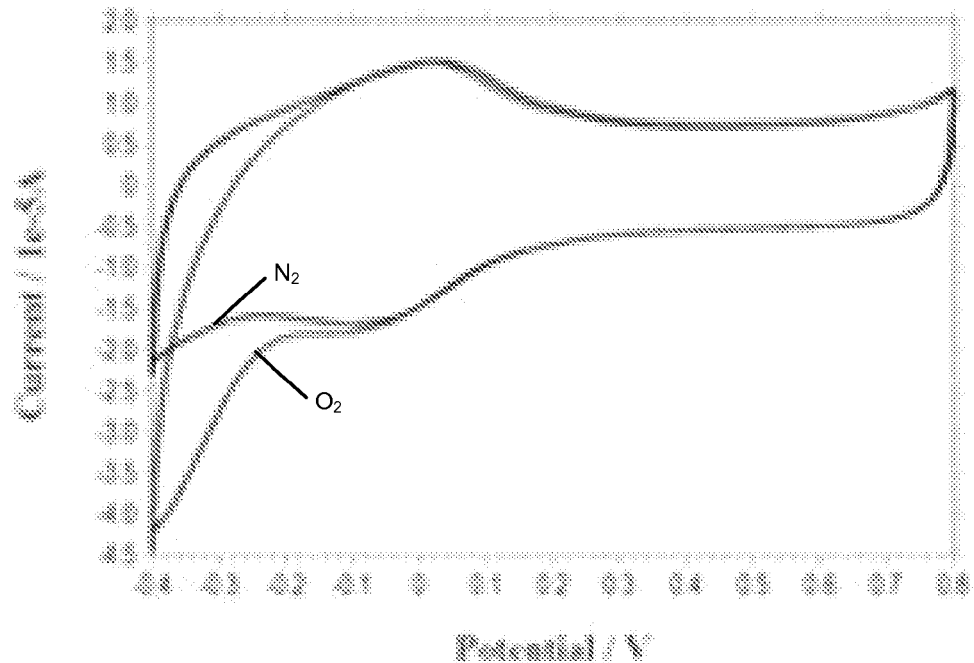
Figure 5C:
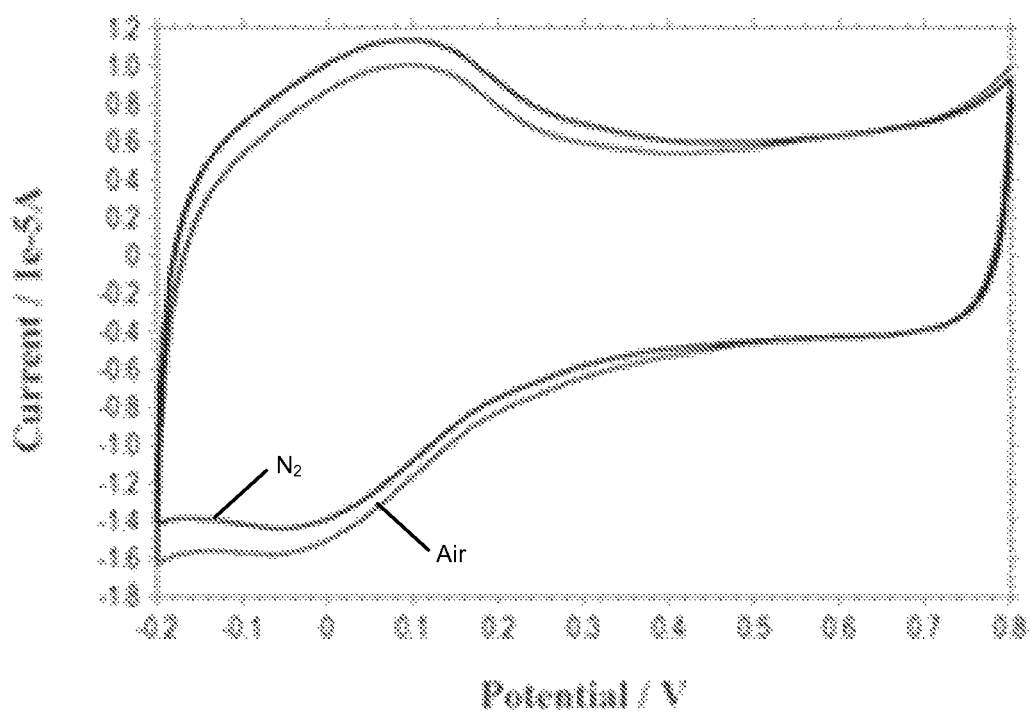

FIGS. 5A-5C show I-V data plots demonstrating the catalytic ability of exemplary biofuel cell devices. FIG. 5A shows a data plot of the current vs. voltage response of an exemplary biofuel cell device including a functionalized anode electrode for various concentrations of a biofuel glucose. For example, the functionalized anode included multi-wall CNTs attached to the surface of carbon-based ink electrodes with a catalyst glucose dehydrogenase (GDH) covalently attached to the functionalized anode. FIG. 5A shows that the exemplary device can produce increasing current with an increase in glucose levels, e.g., and the data plot includes a hump in the curve produced at positive voltage values that shows a potential difference resulting in a current flow in the device.

FIG. 5B shows a data plot of the current vs. voltage response of an exemplary biofuel cell device including a functionalized cathode electrode in the presence and absence of oxygen in a medium including a biofuel lactic acid. For example, the functionalized cathode included multi-wall CNTs attached to the surface of carbon-based ink electrodes with an enzyme catalyst laccase covalently attached to the functionalized cathode. FIG. 5B demonstrates that the exemplary device can produce a greater catalytic output (e.g., resulting in increasing current produced by the device) in the presence of oxygen, as compared to the a nitrogenized medium substantially without oxygen. The data plot also shows that at increasing negative voltage values of the cathode a potential difference results in an increased current flow in the device.

FIG. 5C shows another data plot of the current vs. voltage response of an exemplary biofuel cell device including a functionalized cathode electrode in the presence and absence of oxygen in a medium including a biofuel bilirubin. For example, the functionalized cathode included multi-wall CNTs attached to the surface of carbon-based ink electrodes with an enzyme catalyst bilirubin oxidase (BOD) covalently attached to the functionalized cathode. FIG. 5C demonstrates that the exemplary device can produce a greater catalytic output (e.g., resulting in increasing current produced by the device) in the presence of oxygen, as compared to the a nitrogenized medium substantially without oxygen. The data plot also shows that at increasing negative voltage values of the cathode a potential difference results in an increased current flow in the device.

Implementations of the disclosed biofuel cell technology can have wide-ranging implications in the healthcare and power generation domains. For example, exemplary biofuel cell devices can be implemented as conformal and paper-thin power sources that can sustain implantable and body-worn medical devices and sensors, which can ultimately lower the cost of healthcare and alleviate the burden on the healthcare provider. Moreover, such devices can also contribute to novel remote power systems that can significantly lower the costs associated with energy generation, e.g., in decentralized locations and developing areas that lack access to conventional fuels. For example, another advantage includes the ability to extract energy from raw human waste and byproducts, which represents a globally beneficial direction in energy generation in almost any locale, e.g., including extremely remote locations. Wastewater/sewage constituents, e.g., such as urea, can be processed as biofuels, thereby offering a means to generate useful levels of power from otherwise useless waste sources with zero emissions.

The disclosed biofuel cell devices and systems are especially well-suited to meet the requirements of field-deployable power generation. For example, using thick-film and roll-to-roll fabrication methodologies, very high power-to-weight ratios are achieved, making the exemplary biofuel cells extremely appealing for body-worn applications. For example, through the utilization of self-healing, cross-linked printed electrodes on flexible substrates, extremely robust and durable biofuel cell devices have been demonstrated that can handle the rigors of field deployment. Moreover, unlike conventional fuel cells which must function at high temperatures to operate efficiently, the exemplary biofuel cells are amenable to operation at ambient temperatures, thus minimizing thermal signatures. Due to its direct-conversion architecture, the exemplary biofuel cells are devoid of moving parts, hence underscoring its durability and zero acoustic footprint, which, along with its lack of a heat signature, can help conceal its presence. Additionally, for example, the exemplary biofuel cells are comprised of biocompatible materials and are completely recyclable, unlike conventional fuel cell devices as well as most batteries and photovoltaic systems.

Exemplary implementations of the fabrication techniques to produce the biofuel cells have demonstrate the capability of mass production. For example, the entrapment of biocatalysts on the anode and/or cathode electrodes and the ability to fabricate these electrodes using high-throughput, low-cost printing paradigms are described. For example, a direct conversion architecture of a biocatalyst-electrode heterostructure can include conducting polymer nanotechnology in order to achieve power densities approaching that of conventional fuel cells. Moreover, the exemplary high-efficiency bioelectronic conversion architecture can obviate the need to incorporate precious metal catalysts (e.g., such as platinum) in the electrode matrix, thereby leading to further cost reduction. The exemplary printed biofuel cell platform represents a scalable fuel cell technology. For example, at least a two-order-of-magnitude cost-reduction can be achieved by implementing the described fabrication techniques of the disclosed biofuel cells, e.g., as compared with existing fuel cells, which can reach price parity with existing battery technologies. For example, implementations of the disclosed technology can effectively bridge the gap between high-performance fuel cells currently employed in exotic applications and requirements for low-cost commercially-viable devices. For example, the disclosed biofuel cells can be compatible with volume-manufacturing techniques.

In another aspect, the disclosed technology includes a wearable epidermal biofuel cell device to provide continuous power generation while worn on a human or other user. In some implementations, the exemplary wearable biofuel cell device can be applied to the wearer's epidermis as a temporary-transfer tattoo and is able to scavenge an ample supply of the biofuel L-lactic acid found in the wearer's perspiration in order to generate power. In this exemplary device, the electrodes of the wearable epidermal biofuel cell can be functionalized with lactate oxidase and platinum black within the anode and cathode, respectively, to achieve the power generating operation. Exemplary implementations of the exemplary wearable epidermal biofuel cell were performed to demonstrate the application of various forms of mechanical deformation relevant to practical epidermal applications, which resulted in minimal effects on the performance of the device. For example, an exemplary implementation of the epidermal tattoo biofuel cell device during a controlled fitness routine revealed a maximum power density of 68 $\mu W\ cm^{-2}$ was obtained, hence realizing power production from human perspiration. The epidermal bioenergy paradigm thus holds noteworthy potential for use in the fitness, sport, athletics, performance, and generalized healthcare monitoring domains.

As the cost of personal health monitoring continues to rise, the fitness and healthcare industries have become increasingly reliant on wearable sensors to quantify various physiological metrics in a non-intrusive, user-friendly, and cost-effective fashion to reduce such costs. For example, for epidermal biosensing applications, durability, light-weight, and intimate skin conformance are core requirements of such sensor devices to assess vital signs, e.g., such as heart rate, respiration rate, oxygenation of the blood, skin temperature, bodily motion, brain activity, and blood pressure, as well as chemical sensors capable of monitoring various physiological analytes on the wearer's epidermis as well as chemical agents in their local vicinity. For example, these conformal electronic and diagnostic technologies have advanced considerably to the point of integration of disparate systems on a single skin-adhesive substrate. However, further progress in this arena has been hindered by the lack of wearable and conformal power sources, especially those able to harness the mechanical or chemical energy produced by the wearer's body. While flexible and thin battery technologies have been developed, toxicity, longevity, device weight, and overall poor operational performance have precluded their use in transdermal applications, as well as the rigorous mechanical deformation encountered during bouts of physical activity remains to be addressed with respect to these devices. Additionally, piezoelectric energy harvesting materials have also been plagued by the low efficiencies associated with the electromechanical interconversion process in crystalline media lacking inversion symmetry. The disclosed wearable epidermal biofuel cell technology can be implemented to circumvent these challenges with conventional power sources and provide continuous extraction of biochemical fuels from the wearer's epidermis, which can further enable the development of epidermal electronics that can be utilized in the field.

Exemplary implementations of exemplary wearable epidermal biofuel cell devices were performed that demonstrated the ability to generate useful levels of power from the perspiration of live subjects in a non-invasive and continuous fashion through the use of temporary-transfer tattoos. In some implementations, this was accomplished via the selective oxidation of lactate present in the wearer's perspiration through the inclusion of the enzyme lactate oxidase in the anode matrix in conjunction with the water-insoluble electrochemical mediator tetrathiafulvalene (TTF). For example, lactic acid is the most abundant molecular constituent of the perspiration and is also a widely-recognized indicator of exercise intensity, muscular exertion, fatigue, and aerobic/anaerobic respiration. Charting lactate levels in real-time can thus yield timely information regarding an individual's metabolic response to a fitness routine, hence enabling the individual, trainer, coach, and/or healthcare provider to quantify performance levels. Advantageously, an individual's fitness levels and aerobic capacity can indirectly be inferred by the amount of current (and hence power density) produced by the device.

The disclosed tattoo biofuel cell devices address the requirements imparted by epidermal wear, e.g., including, but not limited to, the ability of the device to maintain its structural and electrochemical resiliency against repeated (and often severe) mechanical deformation such as sheer stress and strain. For example, the exemplary tattoo biofuel cell devices can include dispersed carbon fibers within the ink used to print the anode and cathode electrodes, multi-walled carbon nanotubes incorporated in the electrode contingents to facilitate electron transfer, as well as the immobilization of the catalyst (e.g., lactate oxidase) entrapped in a biocompatible chitosan membrane, which synergistically results in the fabrication of biofuel cells that are largely impervious to mechanical strain, stress, and degradation associated with epidermal wear. For example, operation of the exemplary tattoo biofuel cell devices can produce a redox current from the direct oxidation of lactate within the perspiration via biocatalysis at the anode (and concomitant catalytic reduction of oxygen at the cathode) to generate electrical energy at a load. As such, the disclosed tattoo biofuel cell devices can be implemented in a number of practical applications to satisfy the energy requirements of epidermal, transdermal, and percutaneous devices.

Exemplary materials and methods to implement the disclosed embodiment of the technology are presented. The following chemicals and reagents were used in the described implementations, which included tetrathiafulvalene (TTF), glutaraldehyde solution (8%), chitosan, Pt black, bovine serum albumin (BSA), lactic acid, glucose, potassium phosphate monobasic ($KH_2PO_4$), potassium phosphate dibasic ($K_2HPO_4$), hydrochloric acid (HCl), ammonium hydroxide ($NH_4OH$), sodium chloride (NaCl), potassium chloride (KCl), calcium chloride ($CaCl_2$), magnesium chloride ($MgCl_2$), and sodium bicarbonate ($NaHCO_3$), which were obtained from Sigma-Aldrich. Lactate oxidase (LOx) was obtained from Toyobo Corp. (Osaka, Japan), and carboxy-functionalized multi-walled carbon nanotubes (MWNTs-COOH) were obtained from cheaptubes.com (Brattleboro, Vt.). All reagents were used without further purification. Carbon fibers (e.g., 8 μm diameter, 6.4 mm length, 93% purity) were obtained from Alfa Aesar (Ward Hill, Mass.), and further processing was performed to reduce their length to approximately 2 mm.

The fabrication of the exemplary tattoo biofuel cells used in the described implementations included the following processes and procedures, which were utilized in exemplary demonstrations and implementations of the disclosed embodiment under exemplary conditions disclosed herein. Design of the temporary transfer tattoo pattern was accomplished in AutoCAD (Autodesk, San Rafael, Calif.) and fabricated on 75 μm-thick stainless steel through-hole and mesh stencils (Metal Etch Services, San Marcos, Calif.). Unique stencil patterns were used for each layer printed. Chopped carbon fibers were dispersed within a conductive carbon (E3449) ink (Ercon, Inc, Wareham, Mass.) to increase the tensile strength of the electrode. Printing was performed using an MPM-SPM semi-automatic screen printer (Speedline Technologies, Franklin, MA). Blank temporary transfer tattoo paper and the accompanying adhesive substrate (Papilio, HPS LLC, Rhome, Tex.) was used.

Figure 6:
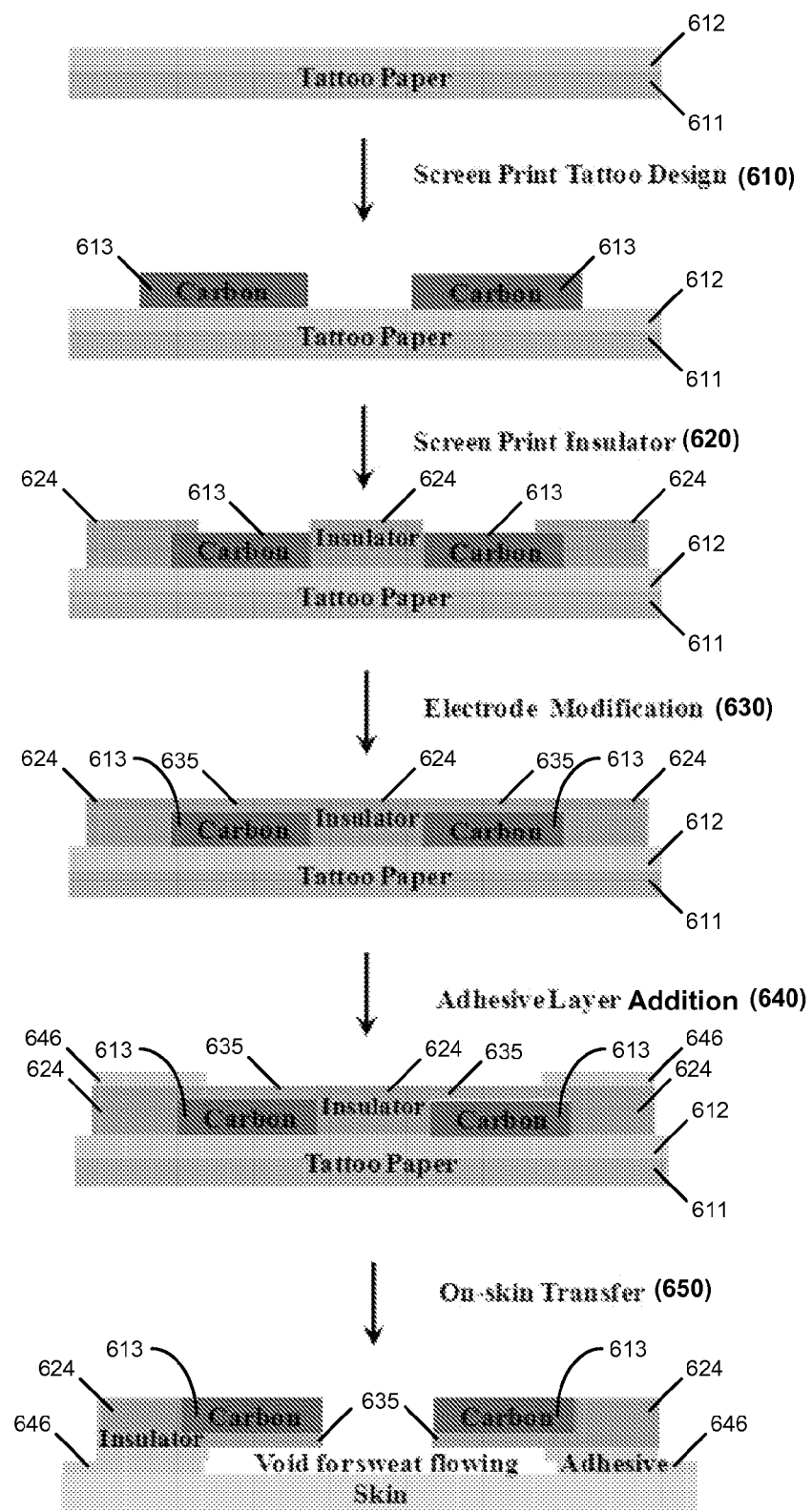
FIG. 6 shows a schematic illustration of an exemplary tattoo biofuel cell fabrication process.

FIG. 6 shows a schematic illustration of an exemplary method to fabricate tattoo biofuel cells using screen printing techniques. The fabrication method includes a process 610 to deposit electrodes 613 on a tattoo paper substrate comprising a release agent 612 coated on a base paper 611. For example, the release agent 612 can include hydrophobic material that releases upon exposure moisture, e.g., such as polydimethylsiloxane (PDMS), a cellulosic-based material, a silicone material, among others. For example, the electrodes 613 can formed by screen printing, roll-to-roll printing, aerosol deposition, inkjet printing, or other printing techniques to fabricate a printed anode and cathode of the tattoo biofuel cell device. The electrodes 613 can be formed of a carbon-based ink material or other electrically conductive material, which can include a catalyst, e.g., including, but not limited to, an enzyme biocatalyst or noble metal catalyst, dispersed within the ink. Implementation of the process 610 to deposit the electrodes 613 can also include the formation of interconnects, contact pads, or other electrical components of the tattoo biofuel cell device. The process 610 can include a curing procedure to thermally or UV cure the electrodes 613 on the tattoo paper substrate material. In some implementations, the process 610 can include the deposition and curing of an underlayer of an electrically conductive material, which can include the interconnects, contact pads, or other electrical components of the tattoo biofuel cell device. The fabrication method includes a process 620 to deposit a layer of a transparent insulator material 624 on the tattoo paper substrate exposing the electrodes 613. The fabrication method includes a process 630 to modify the electrodes 613 with a biochemical modifier 635. In some implementations, the process 630 can include attaching the catalyst as the biochemical modifier 635 to the anode and/or cathode by coating the catalyst as a layer on the surface of the anode and/or cathode electrode; by entrapping the catalyst in an electropolymerized conducting polymer formed on the surface of the anode and/or cathode electrode; by entrapping the catalyst using a selectively permeable scaffold-like structure, e.g., such as an electro-permeable membrane, formed on the surface of the anode and/or cathode electrode; by covalently bonding the catalyst to the surface of the anode and/or cathode electrode; or by electrostatically anchoring the catalyst to the surface of the anode and/or cathode electrode. In some implementations, the process 630 can include attaching an electroactive mediator as the biochemical modifier 635, in addition to or alternatively to the catalyst, to the anode and/or cathode electrode using any of the described techniques. The fabrication method includes a process 640 to deposit an adhesive layer of an adhesive material 646 over at least a portion of the transparent insulator material 624 on the tattoo paper substrate, e.g., still exposing the electrodes 613, to produce the tattoo biofuel cell device ready for implementation and wearable on a user's body. For example, subsequent to the fabrication method, the tattoo biofuel cell device can be attached to a user in an on-skin transfer process 650, in which the adhesive layer is directly attached to the skin and the tattoo paper substrate is peeled off of the device by removing the release agent 612 (e.g., which also removes the base paper 611). For example, in some implementations, the fabricated tattoo biofuel cell device can include a void region to permit sweat or other substance including the biofuel to flow.

The two electrode constituents of the tattoo biofuel cell were designed in the shape of 'UC' (acronym for the University of California). As shown in FIG. 6, the entire contingent was printed on the tattoo base paper using carbon fiber-reinforced (1.5% wt.) carbon ink via the thick-film screen printing fabrication process utilizing the stencil set. This was followed by the screen printing of a transparent insulator (Dupont 5036, Wilmington, Del.) on top of the carbon electrodes. The stencil employed for the transparent insulator ink was designed to insulate all but the active areas of the two electrodes. Following every screen printing step, the printed tattoo paper was cured at 90° C. for 15 min in a convection oven.

Following the fabrication of the tattoo BFC, the anode ('U') was modified with LOx while the electrode 'C' was functionalized with Pt black to serve as the cathode. With respect to the bioanode modification, a suspension of carbon nanotubes in ethanol (5 mg/mL) was sonicated for several hours, and then mixed with 0.1 M TTF ethanol/acetone solution in a 2.0:1.6 volume ratio. The suspension was subsequently cast onto the open area of the anode. After the electrodes completely desiccated, 5 µL LOx solution (40 mg/mL with 10 mg/mL BSA) was cast on the electrode, and then covered with 2 µL of 1 wt % chitosan solution. The electrodes were then cross-linked with glutaraldehyde vapor and stored at 4° C. overnight. To modify the tattoo BFC cathode, an aqueous solution of 10 mg/mL Pt black was sonicated and 10 µL of the suspension was cast on the electrode. Following complete desiccation, 1 µL Nafion solution (5 wt %) was cast on the electrode to act as a protective layer.

As illustrated in FIG. 6, in order to transfer the tattoos to a substrate, a transparent adhesive sheet was first applied to the tattoo paper, which ensured that the tattoo adhered satisfactorily to the body/substrate. A rectangular region was excised from the adhesive sheet such that the active anode and cathode areas remained unobstructed to enable the facile diffusion of lactate and oxygen to the respective electrode contingents. In order to apply the adhesive layer to the substrate, one of the transparent protective sheets from the adhesive sheet was removed and the adhesive layer was first mated with plain tattoo base paper. Later, the second transparent protective sheet mated with the adhesive sheet was removed to expose the adhesive layer. A void was also left between the anode and cathode contingents to facilitate the flow of perspiration between these two components. Next, the tattoo contingent was applied to the substrate, the base paper was dabbed with water to dissolve the release agent, and the wet base paper was gently removed to expose the adhesive layer on the substrate. The tattoo BFC was finally placed on the adhesive sheet already located on the substrate and removed by dabbing it with water and gently peeling the base paper from the substrate.

In one exemplary embodiment of the disclosed tattoo biofuel cell device, an epidermal biofuel cell device includes a substrate formed of a flexible electrically insulative material structured to adhere to the skin of a user, an anode formed on the substrate of an electrically conductive material, the anode including a catalyst to facilitate the conversion of a fuel substance in a biological fluid to a first product in an oxidative process that releases electrons captured at the anode, thereby extracting energy from the fuel substance, a cathode configured on the substrate adjacent to the anode and separated from the anode by a spacing region, the cathode formed of a material that is electrically conductive and capable of reducing an oxygenated substance in the biological fluid to a second product in a chemical reduction process in which the second product gains electrons, and an anode electrode interface component and a cathode electrode interface component formed on the substrate and electrically coupled to the anode and the cathode, respectively, via electrical interconnects, in which the extracted energy is addressable as electrical energy at the anode electrode interface component and the cathode electrode interface component.

Exemplary implementations of the exemplary tattoo biofuel cell device were performed to perfect the device with regards to the electrochemical performance in vitro. For example, the tattoo biofuel cells were first evaluated by transferring the pattern onto a rigid plastic substrate or onto a flexible GORE-TEX textile for mechanical integrity studies. For example, 0.2 M McIlvaine buffer (pH 5.5) was utilized to emulate the average pH value of human perspiration. With respect to in vitro stability evaluation, artificial perspiration was prepared with the following electrolytes, metabolites, and small molecules, e.g., including $Na_2SO_4$, $NaHCO_3$, KCl, $MgCl_2$, $NaH_2PO_4$, $CaCl_2$, acetic acid, lactic acid, pyruvic acid, glucose, uric acid, urea, creatinine and ascorbic acid. The pH of the artificial perspiration stock solution was adjusted to 5.3 by 5 M $NH_4OH$. All solutions were prepared with ultra-pure water (18.2 MΩ·cm). Electrochemical characterization was performed at room temperature leveraging a CH Instruments (Austin, Tex.) model 1232A potentiostat.

Healthy volunteer subjects participated in the exemplary power generation experiments. Each volunteer was instructed to wear a temporary transfer tattoo BFC on their upper bicep in order to assess real-time power generation. The BFC was connected to an external 100 kΩ load resistor ($R_L$) in order to achieve maximum power transfer. This value was selected to most closely match the internal series resistance ($R_s$) such that the maximum power transfer condition was satisfied ($R_s = R_L$). Electrical current was recorded every 5 s using a Keithley (Cleveland, Ohio) 6514 system electrometer interfaced with a computer system including at least a processor and a memory unit including a control program (e.g., instructions in Matlab) to continuously process acquired current readings via the GPIB interface and interpolated the concomitant power generated per unit area ($P_{DENSITY} = I^2 R_L / A_E$, $A_E = 0.06$ cm$^2$). In order to filter extraneous noise, a 10-point moving average was iterated at each data point. For example, the subjects were instructed to mount a stationary cycle and a heart rate (HR) monitor was employed to track the subjects' HR. Subjects were instructed to begin cycling at a steady, slow cadence for 3 min. Following this 'warm-up' period, subjects were instructed to cycle at an increasing pace until 80% of their maximum heart rate was achieved in order to ensure that the anaerobic respiration threshold was attained, hence augmenting the excretion of lactic acid in the perspiration. Immediately following the subjects' transition to the anaerobic regime, the subjects were instructed to maintain their current cadence for 15 min in order to observe the temporal evolution of the lactate level. Following the 15 min intense exercise activity, subjects were instructed to gradually reduce their cadence during a 3 min 'cool-down' period. The volunteers ingested no fluid (dehydrated state) prior to and during the duration of the fitness routine.

Figure 7:
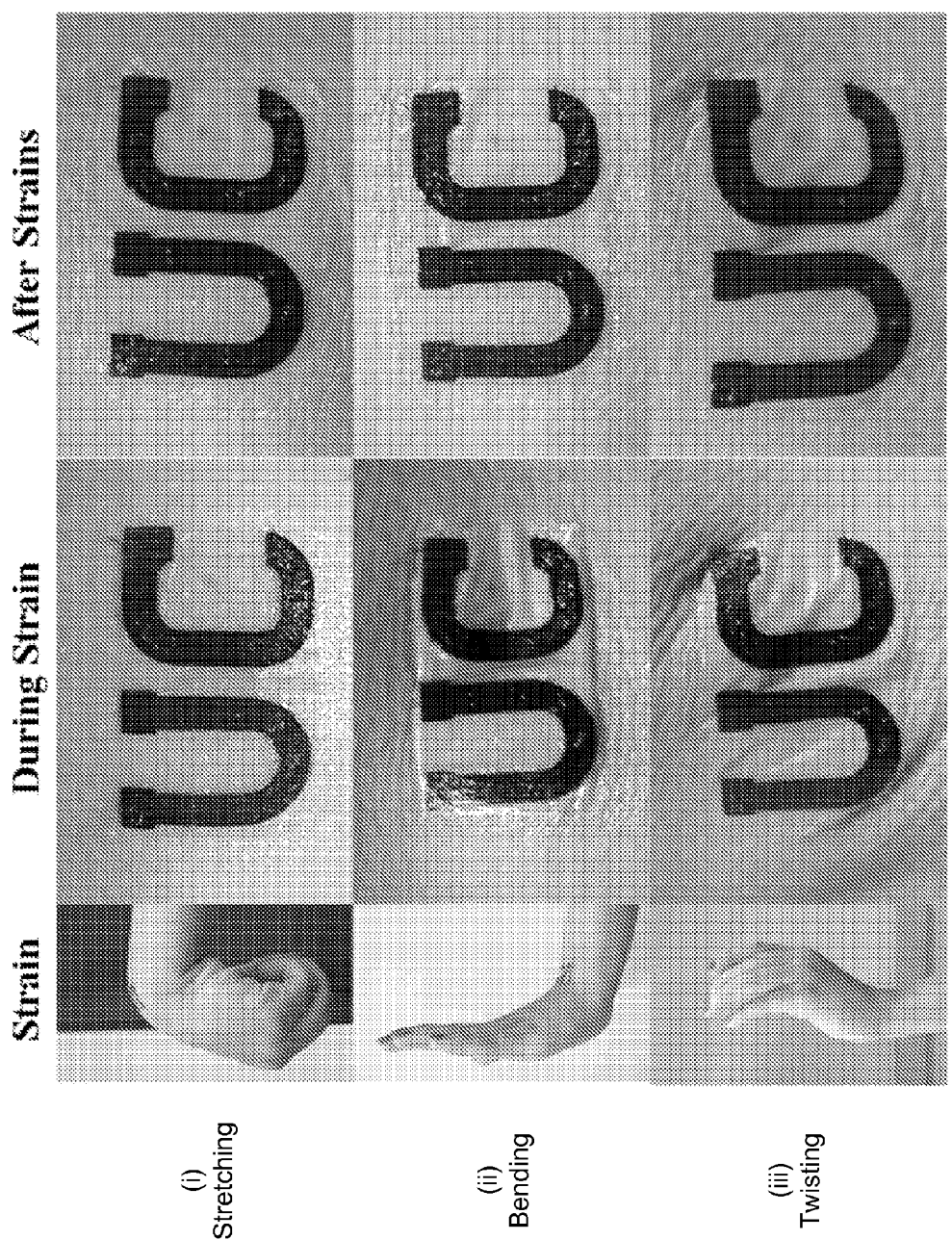
FIG. 7 shows images of mechanical strain implementations on a human wrist of an exemplary tattoo biofuel cell device during and after stretching, bending, and twisting.

Exemplary implementations of exemplary wearable epidermal biofuel cell devices were performed that demonstrated resiliency against mechanical stress caused by continuous body movements. For example, the longevity of such epidermal-mounted devices depend greatly on their ability to adhere well to the human skin without developing fractures that damage the devices. The most common body movements involve flexions, which typically comprise of bending, stretching, and/or twising of the epidermal layer. Accordingly, such devices must encompass an intrinsic flexibile and stretchable nature in addition to being able to adhere well to the epidermis. The disclosed tattoo biofuel cell devices include dispersion of carbon fibers within the inks employed to print these devices, which provide a conductive, interleaved backbone that aids in maintaining the electrical conductivity under various biomechanical stressors. Similarly, the use of an adhesive layer firmly attaches the tattoo biofuel cells to the skin. Visual analysis of the tattoo biofuel cell device on the dorsal region of a human wrist under repeating bending, stretching, and twisting dorsiflexion movements was performed for a total of 50 iterations. FIG. 7 shows images of the epidermal tattoo biofuel cells during mechanical stress caused by continuous body movements including (i) stretching, (ii) bending, and (iii) twisting. The left column of image in FIG. 7 provides the side view of dorsal movements; the middle column provides images of the top view of the biofuel cell tattoos during the various deformations; and the right column provides images of the top view of the biofuel cell tattoos at the end of each movement. The images demonstrate that the tattoo biofuel cell devices are quite resilient to flexions that emulate epidermal wear, e.g., as a consequence of the overlying insulator layer, which serves to maintain the structural integrity of the printed carbon layer. Accordingly, the epidermal biofuel cell devices can perform desirably under various strains and thus can serve as a compelling platform for various epidermal applications.

To date, the majority of lactate biofuel cells have been based on the lactate dehydrogenase enzyme. However, in these existing devices, $NAD^+$ must be employed as the cofactor, which represents a noteworthy challenge given that this molecule must be immobilized on the electrode to prevent it from leeching into the matrix while being able to diffuse, with relative ease, to the enzyme's active site.

The disclosed technology includes an exemplary lactate-based biofuel cell utilizing the lactate oxidase (LOx) enzyme for non-invasive power generation from human perspiration, e.g., by selectively catalyzing the oxidation of lactate in the perspiration as the biofuel for epidermal power generation. In some implementations the electrodes of the exemplary tattoo biofuel cell device are functionalized to achieve efficient bioelectrocatalytic conversion, e.g., in which the 'U' of the tattoo (anode) was functionalized with MWNTs/TTF/LOx, hence serving as the bioanode to catalyze the oxidation of lactate to pyruvate in the presence of oxygen (cofactor). The cathode 'C' made use of a drop-casted Pt black layer, protected with a Nafion proton-exchange membrane.

An image of the exemplary functionalized device is shown in FIG. 8A. The bioanode of the exemplary tattoo biofuel cell device was functionalized with the mediator TTF and MWNTs. This bioanode was then covered with a layer of chitosan, e.g., a naturally-derived biopolymer well-known for its biocompatibility. For example, chitosan not only serves to protect the modified enzyme electrode, but it also functions as a physical barrier to limit the efflux of the biocatalytic backbone from the tattoo and onto the underlying substrate.

FIG. 8B shows a data plot of polarization curves of the exemplary functionalized MWNTs/TTF/LOx bioanode in the absence of presence of 14 mM lactic acid in 0.2 M McIlvaine buffer solution, pH 5.5, respectively. The electrocatalytic activity of the MWNTs/TTF/LOx bioanode was determined in vitro with an external Ag/AgCl (1 M KCl) electrode and a Pt wire counter electrode. Polarization curves were recorded by applying linear sweep voltammetry with a scan rate of 1 mV/s in McIlvaine buffer pH 5.5 with 14 mM lactic acid, and normalized by the surface area of the electrode as a function of potential. As shown in FIG. 8B, the TTF-mediated oxidation of lactic acid initiates from around −0.1 V with a peak potential of 0.14 V (vs. Ag/AgCl), indicating that the MWNTs/TTF/LOx exhibits selective catalytic ability towards the oxidation of lactic acid, and hence serves as a suitable bioelectrocatalytic cascade for the bioanode constituent of the BFC. For example, TTF can be used a selective mediator to aid in electron transfer between the LOx active site and the electrode surface. Other mediators, e.g., including, but not limited to, derivatives of ferrocene and Meldola's blue, can also be used as the selective mediator of the bioanode. It is noted that although able to mediate the electro-oxidation of lactic acid, these other small-molecule mediators are water-soluble, and the oxidation current obtained may be decayed as a consequence of the leaching of the mediator. Compared with these mediators, TTF encompasses several noteworthy advantages, namely lower oxidation potential and more stable performance. Also, the incorporation of MWNTs further shifted the lactic acid oxidation onset potential more negatively and further enhanced the oxidation current, which may be due to the electron donor-acceptor interaction between TTF and negatively charged MWNTs, resulting in facilitated electron transfer to the electrode. Therefore, the MWNTs/TTF/LOx cascade is well-suited to serve as the bioanode, and, together with a Pt black cathode, a complete lactic acid biofuel cell can be assembled on the exemplary temporary transfer tattoo substrate.

FIG. 8C shows a data plot of power density achieved from the exemplary tattoo biofuel cell device with different lactic acid concentrations. As shown in the figure, the exemplary tattoo biofuel cell device approached 25 $\mu W\ cm^{-2}$ with 8 mM lactic acid (dissolved in buffer), and increased to 34 and 44 $\mu W\ cm^{-2}$ with further increased lactic acid concentrations of 14 mM and 20 mM, respectively. A small signal was observed during control experiments (no lactic acid added).

Figure 9A:
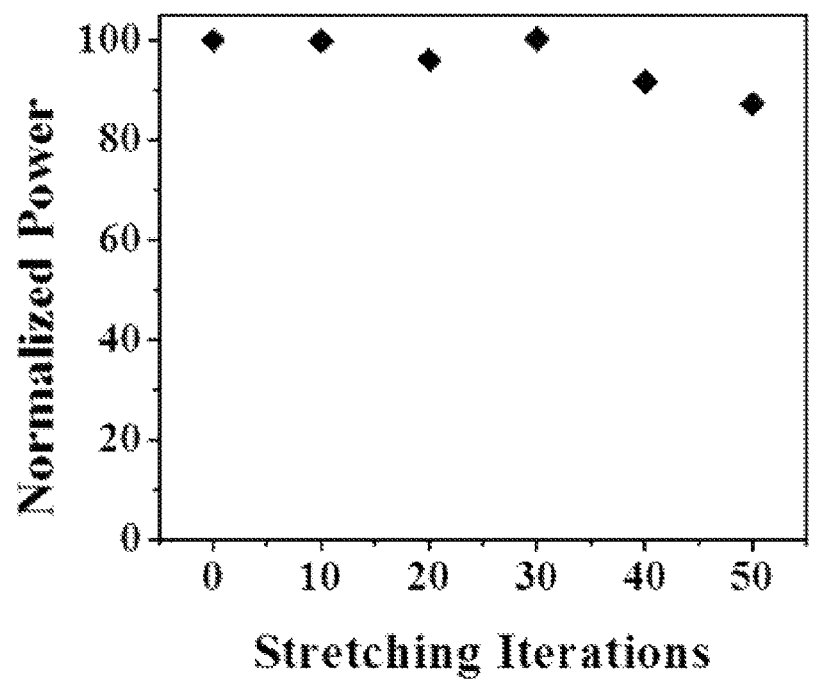
FIGS. 9A and 9B show data plots of the power exhibited by exemplary tattoo biofuel cell devices under repeated stretching and bending.

The exemplary implementations of the exemplary biofuel cell devices included evaluating the mechanical resiliency of the tattoo biofuel cell device in vitro on a GORE-TEX textile. The electrocatalytic behavior of the tattoo biofuel cell device was studied under repeated bending and stretching iterations. With respect to the stretching study, the power output was firstly measured prior to the application of any stress/strain using a fuel containing 14 mM lactic acid in 0.2 M McIlvaine buffer solution, pH 5.5. Thereafter, the tattoo biofuel cell device was stretched ~10% for 5 sec and then relaxed for another 5 sec. This was iterated 10 times, after which the power output was measured using the 14 mM lactic acid fuel solution. Five such cycles were performed until the tattoo biofuel cell device was stretched a total of 50 times. FIG. 9A shows a data plot delineating the electrochemical behavior of the exemplary tattoo biofuel cell device under such stretching deformation. The data plot of FIG. 9A corroborates that the exemplary tattoo biofuel cell device is able to withstand repeated stretching characteristic of epidermal wear. Specifically, for example, the tattoo biofuel cell device, on an average, lost less than 20% of its original power output following 50 stretching iterations.

Figure 9B:
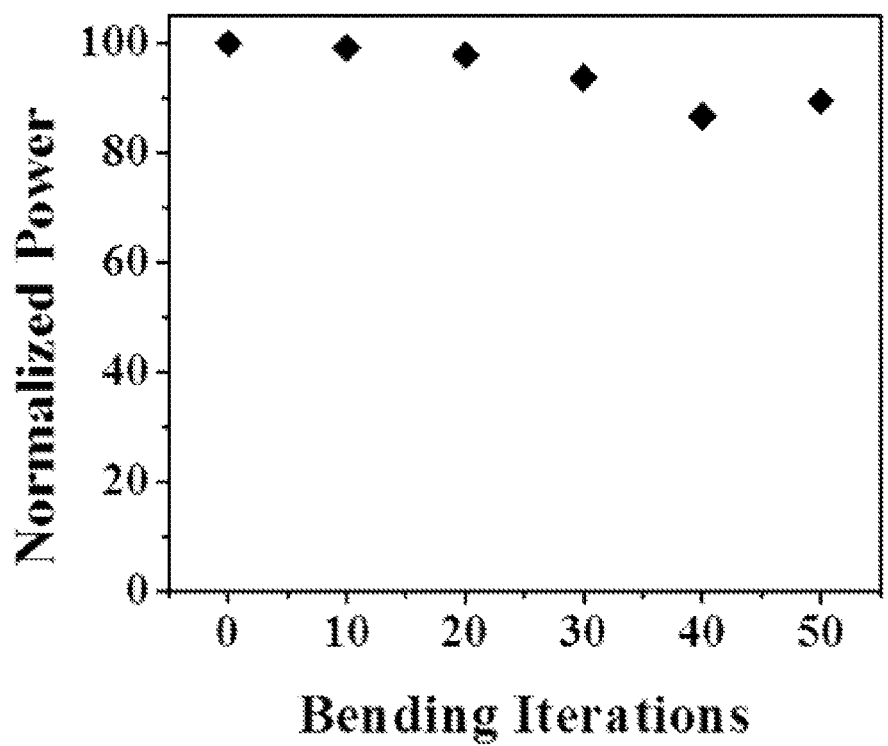

In another exemplary implementation, the electrochemical behavior of the tattoo biofuel cell device was assessed by subjecting it to repeated bending iterations to emulate the application of the device near joints on the human body. During the experiment, the exemplary tattoo biofuel cell device was bent at 90° for 5 sec followed by subsequent relaxation for another 5 sec. The bending and subsequent relaxation of the tattoo was iterated ten times after which the power output was measured. As depicted in FIG. 9B, the exemplary tattoo biofuel cell device exhibited minimal decrement in its efficiency following the application of repeated bending. During both bending and stretching implementations, it was observed that the tattoo biofuel cell device maintained both its structural and electrical integrity. The data plots of FIGS. 9A and 9B substantiate that the exemplary devices encompass the ability to maintain their power output performance in the face of complex stretching and bending deformations, which are typical of epidermal applications.

Figure 10A:
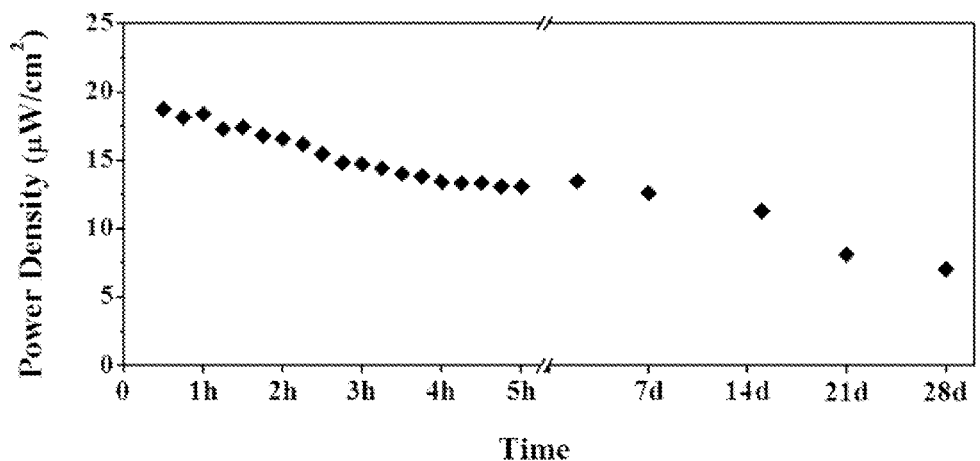
FIGS. 10A and 10B show data plots of the time-dependent power stability of exemplary tattoo biofuel cell devices.
Figure 10B:
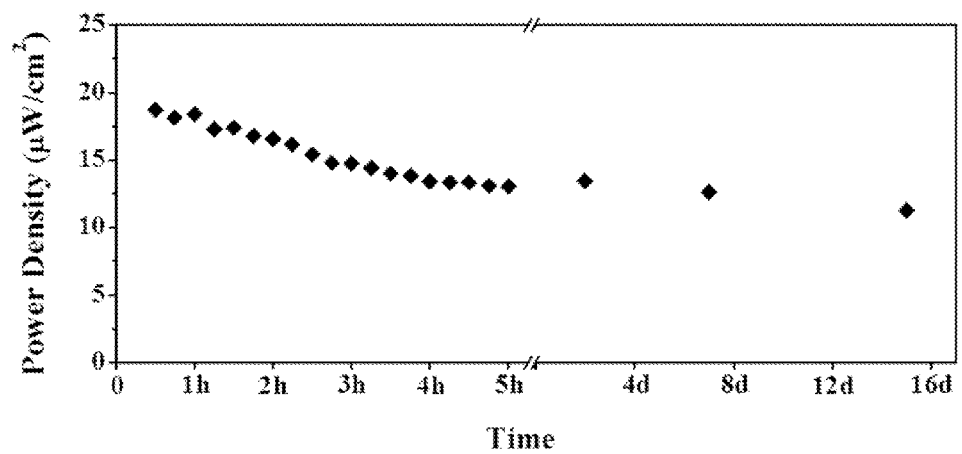

The exemplary implementations of the exemplary biofuel cell devices included evaluating the endurance of the tattoo biofuel cell device under extended durations. For example, prolonged stability of any enzymatic electrode represents a crucial prerequisite for successful long-term use of a biofuel cell. The stability of the exemplary tattoo biofuel cell was studied in vitro using artificial perspiration containing 14 mM lactic acid at pH 5.3, e.g., which represent average values in the human perspiration. The power output was measured continuously for the first 5 hours and then recorded at fixed intervals until 4 weeks had transpired. As shown in FIGS. 10A and 10B, the power output decreased gradually during the first 5 h continuous operation and stabilized to approximately 13 $\mu W\ cm^{-2}$ at the end of this period. It is noted that, for example, as compared with the results obtained in buffer, the power generated in artificial perspiration was notably reduced, which may be due to the high ionic strength of the media as well as matrix effects that can interfere with enzymatic activity or adsorb onto the electrode surface. Nevertheless, the exemplary tattoo biofuel cells remained active even following 4 weeks of use (as shown in FIG. 10A), e.g., decreasing by less than 10% in the initial 7 day period. 50% of the initial power output was measured at the conclusion of the 4-week experimental investigation. Synthesizing these exemplary results, the tattoo biofuel cell devices remain relatively stable for considerable duration and can operate for extended periods of time without compromising performance.

Figure 11A:
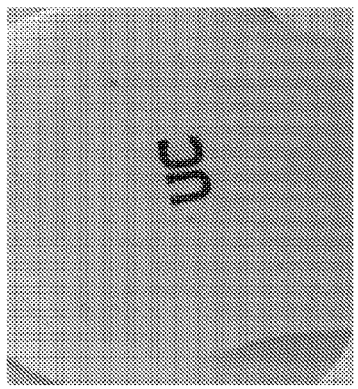
FIG. 11A shows an image of an exemplary tattoo biofuel cell device on the upper arm of a user.
Figure 11C:
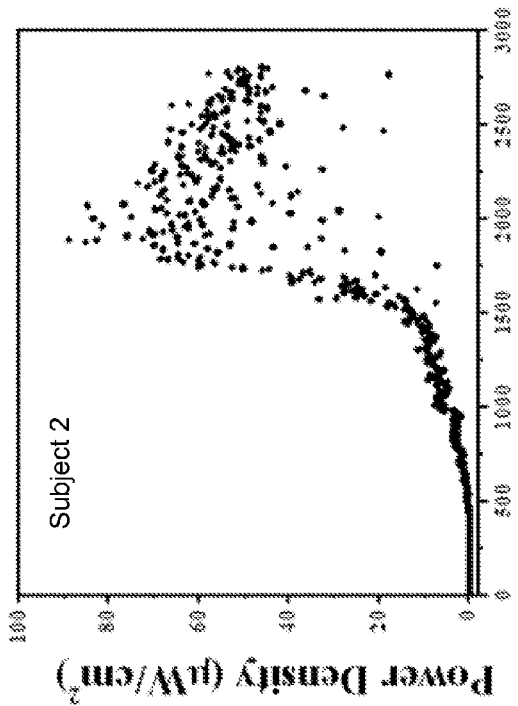
FIGS. 11B-11F show data plots of real time power density measurements of the exemplary tattoo biofuel cell device during cycling exercise.
Figure 11B:
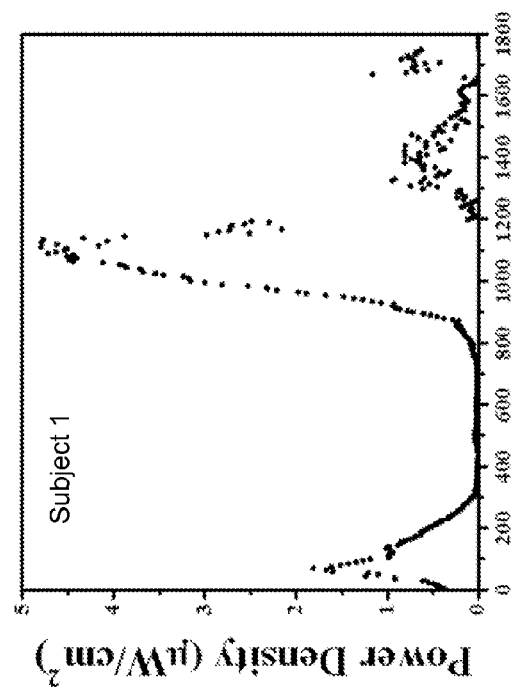
Figure 11D:
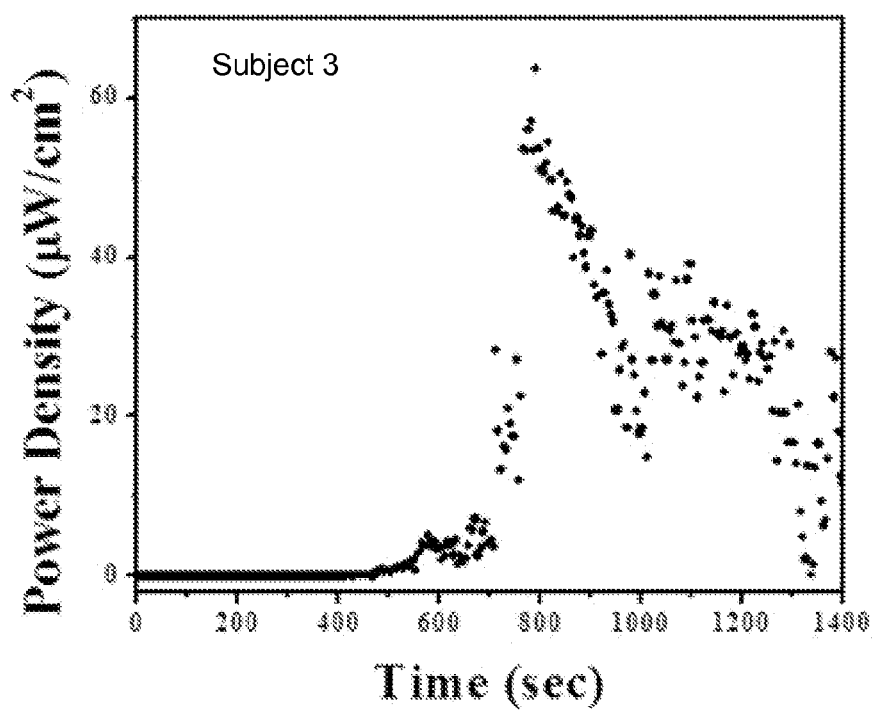
Figure 11E:
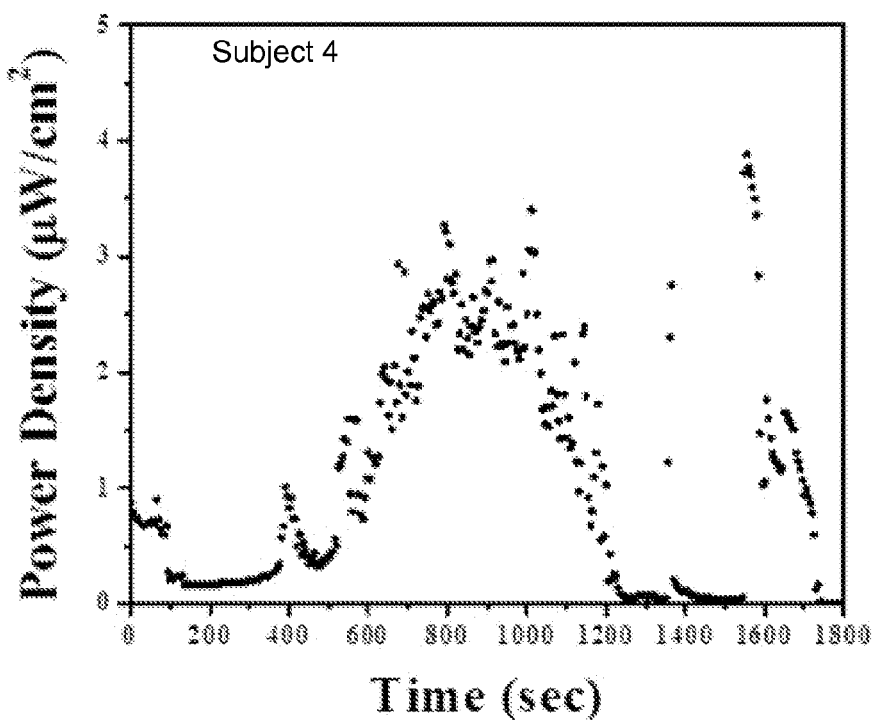
Figure 11F:
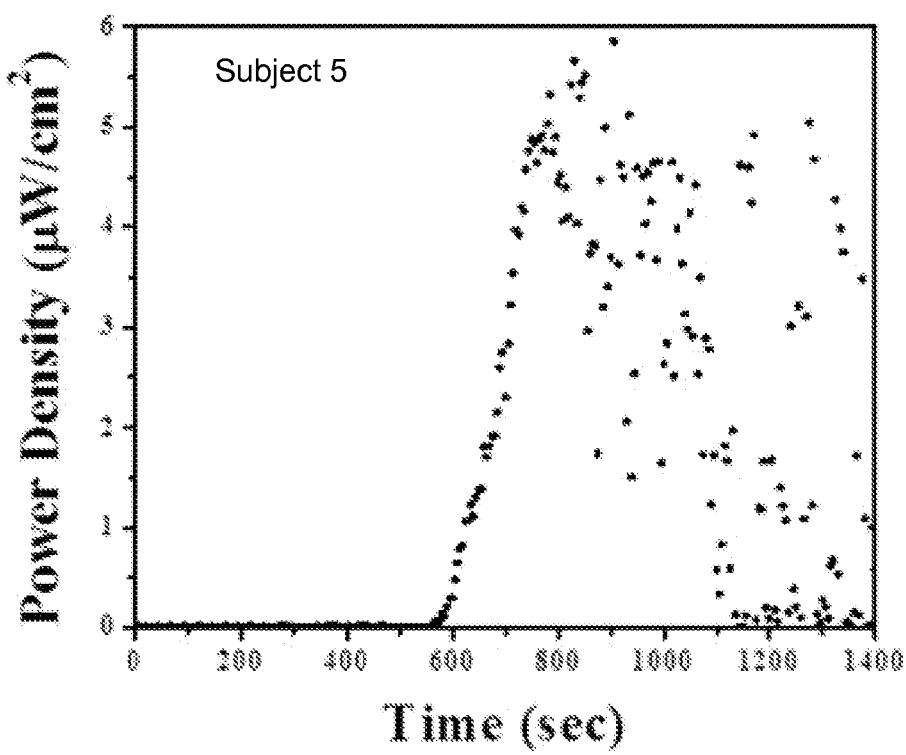

For example, it is known that during intense physical activity the aerobic metabolism is incapable to satisfy the body's energy demands. Under such conditions, the human body instigates the anaerobic metabolism, which is more efficient, thereby providing the body with energy via the glycolytic breakdown of blood glucose and glycogen in the sweat gland to form lactate. As a result, the sweat lactate concentration depends greatly on the intensity of the physical activity pursued, with higher levels corresponding to increased muscular exertion during periods of anaerobic exercise. Additionally, sweat lactate concentration decreases locally due to dilution caused by high sweat excretion rate, which would lead to low power output. As shown in FIG. 11A, the exemplary tattoo biofuel cell devices were applied to subjects' right deltoid, as exemplified in the image, in which the deltoid region remains mostly unperturbed during cycling and thus is suitable for the attachment of leads to the recording instrumentation utilized in the exemplary implementation of the device.

FIGS. 11B-11F show data plots of real time power density of the exemplary tattoo biofuel cell device measured in situ from five exemplary subjects during cycling exercise. It is noted that in all the cases shown in FIGS. 11B-11F, the initial power production during the first three minutes (180 seconds, corresponding to the warm-up session) is negligible. Upon embarking the intense workout session, each subject began perspiring within five to ten min (300 to 600 sec). It was observed that there was a visible increase in the power output when the subjects started sweating, e.g., indicating the increased production of lactate by eccrine sweat glands, and the electrode areas were wetted by the moist to form electron pathway. The lactic acid level in sweat achieves highest at the beginning, and then decreases due to the dilution in larger perspiration. The power output follows the same trend, increased to highest and leveled off and decreased with more intense exercise. The maximum power generation as high as 70 and 55 $\mu W\ cm^{-2}$ were obtained for two of the exemplary subjects who had relative moderate perspiration rates. For subjects with intense cycling and high sweating rate, the power outputs were usually less than 10 $\mu W\ cm^{-2}$, and some of the in situ data were dramatically fluctuating due to intense movements and rapid sweat flow rate. In the exemplary implementations, the power generation for each subject depended on an individual's anaerobic metabolic activity and sweat rate. High power output was observed in cases where the subject had low perspiration rate, while volunteers with high sweat rate produced lower electrical power. This observation of the exemplary data of these exemplary implementations can be attributed to the fact that high sweat rate leads to dilution of lactate thus reducing the biofuel supply to the biofuel cell and limiting the contact time for redox reactions on the electrodes.

Figure 11G:
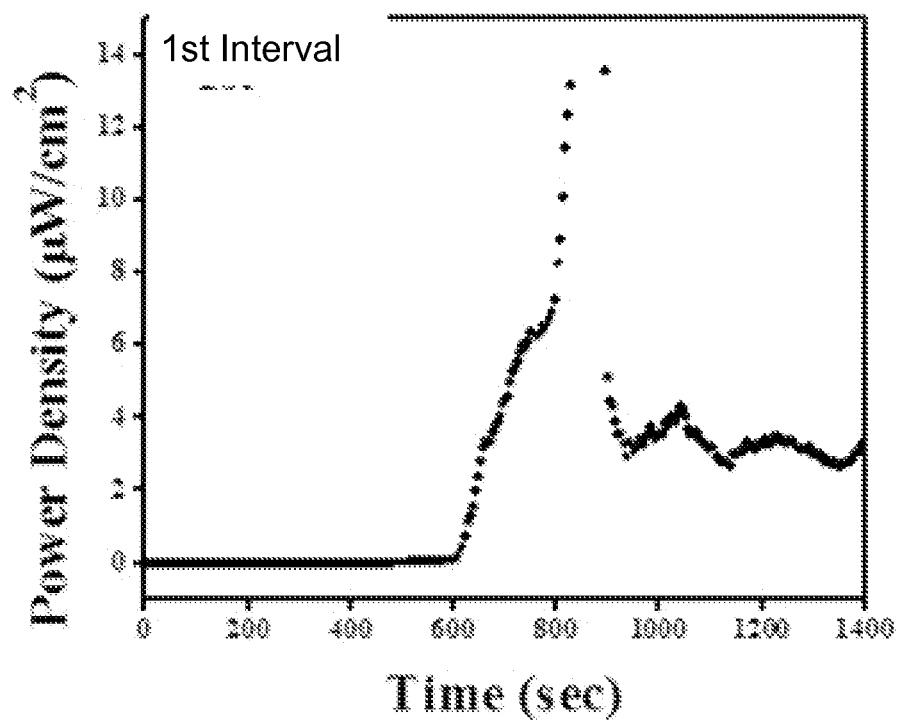
FIGS. 11G-11I show data plots of power output measurements from the exemplary tattoo biofuel cell device with 3 h intervals.
Figure 11H:
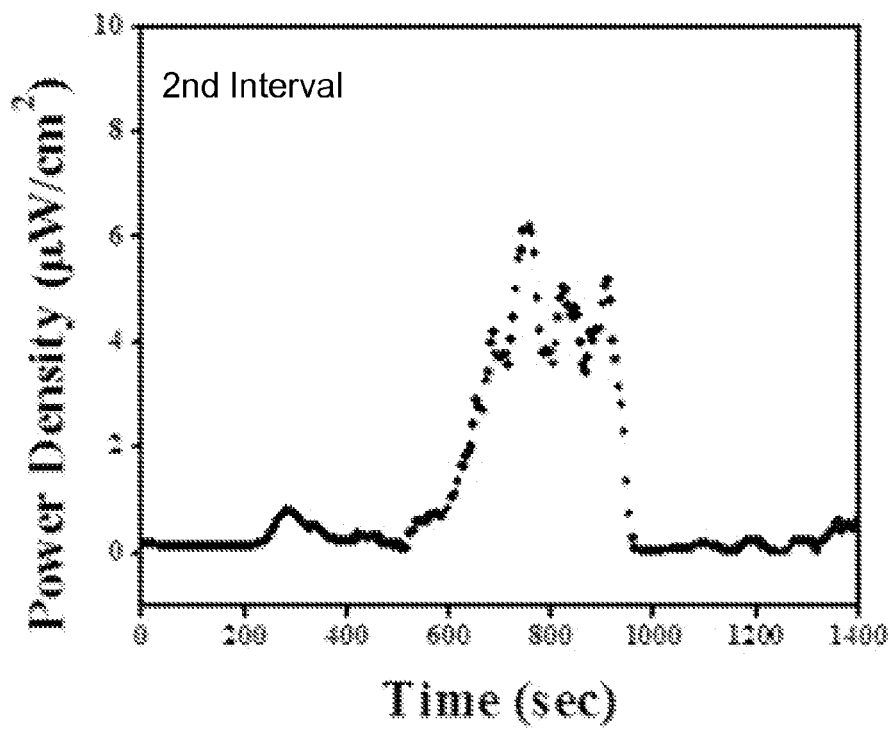
Figure 11I:
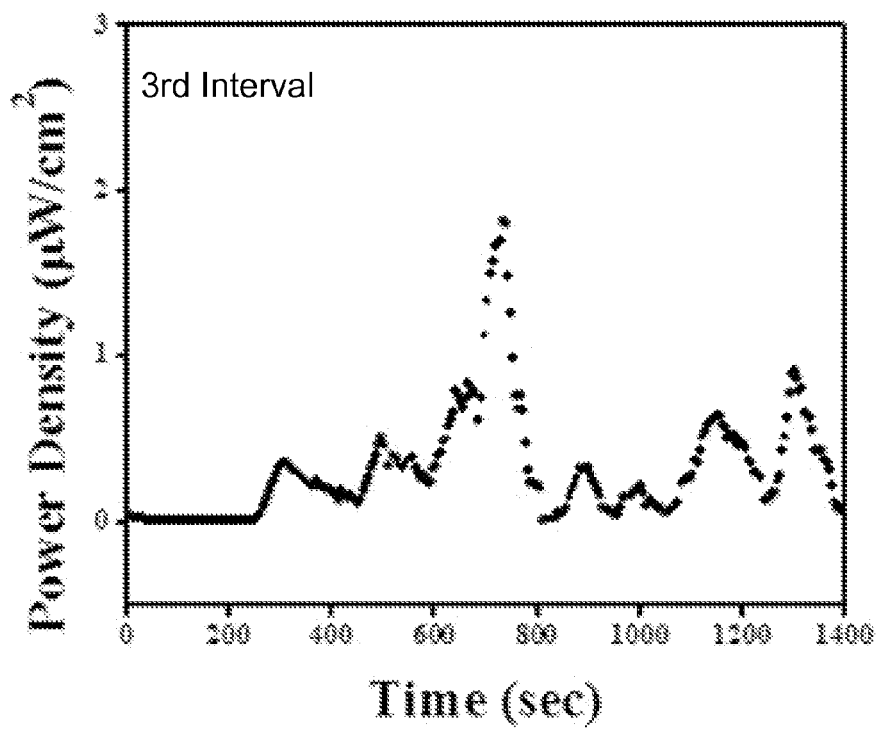

Concomitantly, the exemplary tattoo biofuel cell devices were evaluated over a period of 6 h while it was applied to the subjects' upper bicep. One exemplary subject was instructed to perform 20 min bouts of intense cycling separated by 3 h intervals of rest. FIGS. 11G-11I show data plots of power output measurements from the exemplary tattoo biofuel cell device with 3 h intervals. The data plots of FIGS. 11G-11I demonstrate that the tattoo biofuel cell device has the capability to perform for extended periods of time. The exemplary tattoo biofuel cell device is shown to achieve similar level of power generation compared with the initial exercise.

The ability to extract chemical fuels from human perspiration using a biofuel cell in order to generate power from physical activity has been described. The disclosed technology leverages innovations in printed electrodes fabricated on temporary transfer tattoo substrates in order to achieve the selective bioelectrocatalysis of lactic acid present in a wearer's perspiration in a completely non-invasive fashion. The disclosed tattoo biofuel cell devices intimately conform to the anatomical features of the wearer's skin and maintain structural resiliency under the rigors of on-body use, both core requirements of such devices under practical embodiments of epidermal wear. Advantageously, for example, the tattoo can be designed in any geometry and can be concealed in rather inconspicuous artwork. For example, during some implementations, a power density of 50 $\mu W\ cm^{-2}$ with 20 mM lactic acid in buffer was achieved during repeated trials. Depending on the physical fitness level of the wearer, power ranges during these exemplary implementations ranged from 3 to 68 $\mu W\ cm^{-2}$ (e.g., with higher power levels corresponding to less fit individuals), hence underscoring the large dynamic range of lactic acid expected within the perspiration. In addition, the stability of the exemplary tattoo biofuel cell device was implemented with artificial perspiration over a 3-week period, and the power output achieved following this exemplary protracted study was 50 percent of the original value, further accentuating the extended-term stability of the disclosed biofuel cell devices. The amalgamation of the disclosed biofuel cell technology can address the power requirements of in-the-field wearable sensors and other devices.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A biofuel cell device, comprising:
 a substrate;
 an anode disposed on the substrate of an electrically conductive material, the anode including a catalyst to facilitate the conversion of a fuel substance in a biological fluid to a first product in an oxidative process that releases electrons captured at the anode, thereby extracting energy from the fuel substance;
 a cathode disposed on the substrate adjacent to the anode and separated from the anode by a spacing region, the cathode formed of a material that is electrically conductive and capable of reducing an oxygenated substance in the biological fluid to a second product in a chemical reduction process in which the second product gains electrons; and
 a load including one or more electrical circuit elements electrically coupled between the anode and the cathode to obtain the extracted energy as electrical energy;
 wherein one or both of the anode and the cathode includes a carbon-based ink material;
 the device further comprising a first layer and second layer each formed of an electrically conductive material on the substrate and underneath the anode and cathode, respectively, the first layer and second layer separated from one another.

2. The device of claim 1, wherein the substrate includes an electrically insulative and flexible material.

3. The device of claim 1, wherein the biological fluid includes at least one of perspiration, blood, urine, saliva, or lacrimal fluid, or wherein the fuel substance includes at least one of glucose, alcohol, lactic acid, urea, uric acid, or ascorbic acid, or wherein the catalyst includes at least one of glucose oxidase, lactate oxidase, urate oxidase, or ascorbate oxidase.

4. The device of claim 1, further comprising a container on the substrate structured to contain the biological fluid in a region surrounding the anode and the cathode.

5. The device of claim 1, wherein one or both of the anode and the cathode further includes carbon nanotubes.

6. The device of claim 1, wherein the catalyst is encased in a porous scaffold structure formed of a conducting polymer on the surface of the anode, or wherein the catalyst is covalently bound to the surface of the anode, or
wherein the catalyst is entrapped in a selectively permeable membrane coupled to the surface of the anode, or
wherein the catalyst is electrostatically bound to the surface of the anode.

7. The device of claim 1, wherein the anode further includes an electroactive mediator to facilitate electron transfer between an active site of the catalyst and the surface of the anode.

8. The device of claim 1, wherein the cathode includes a noble metal catalyst that is configured in a carbon-based ink material of the cathode or on the surface of the cathode, wherein the noble metal catalyst includes at least one of platinum or palladium.

9. The device of claim 1, wherein the cathode further includes an enzyme to facilitate the reduction of the oxygenated substance in the biological fluid to form the second product.

10. The device of claim 9, wherein the enzyme is encased in a porous scaffold structure formed of a conducting polymer on the surface of the cathode, or
 wherein the enzyme is entrapped in a selectively permeable membrane to the surface of the cathode, or
 wherein the enzyme is electrostatically bound to the surface of the cathode, or
 wherein the cathode includes an electroactive redox mediator to interface an active site of the enzyme with the surface of the cathode, wherein the electroactive redox mediator facilitates the transfer of electrons from the cathode to the active site of the enzyme.

11. A biofuel cell system, comprising:
 a biofuel cell module, including:
  (i) a container structured to include an opening on a top surface and a hollowed interior to contain a fluid including a fuel substance,
  (ii) an array of biofuel cells formed on a flexible substrate and contained in the container, wherein a biofuel cell of the array includes an anode disposed on the flexible substrate of an electrically conductive material, the anode including a catalyst to facilitate the conversion of the fuel substance to a first product in an oxidative process that releases electrons captured at the anode, thereby extracting energy from the fuel substance, a cathode positioned adjacent to the anode on the flexible substrate and separated from the anode by a spacing region, the cathode including a material that is electrically conductive and capable of reducing an oxygenated substance in the biological fluid to a second product in a chemical reduction process in which the second product gains electrons, and electrical interconnects connecting the anode and the cathode to an anode electrode contact pad and a cathode electrode contact pad, respectively, and
  (iii) a first electrical interface and a second electrical interface in electrical connection with the anode electrode contact pad and the cathode electrode contact pad, respectively; and
 a power storage module, including:
  (i) a housing including a releasable attachment component to attach to and detach from the biofuel cell module, wherein the attachment component seals the opening when attached,
  (ii) an electrical storage unit contained within the housing and configured of one or more electrical circuit elements electrically coupled to the first electrical interface and the second electrical interface when the attachment component is attached to the power storage module, the electrical storage unit configured to store the extracted energy as electrical energy, and (iii) an electrical outlet configured on an outer surface of the power storage module and electrically coupled to the electrical storage unit, the electrical outlet structured to electrically interface with a device to provide power to the device.

12. The biofuel cell system of claim 11, wherein the catalyst is attached to the surface of the anode by at least one of: (i) the catalyst is encased in a porous scaffold structure formed of a conducting polymer on the surface of the anode, (ii) the catalyst is covalently bound to the surface of the anode, (iii) the catalyst is entrapped in a selectively permeable membrane coupled to the surface of the anode, or (iv) the catalyst is electrostatically bound to the surface of the anode.

13. The biofuel cell system of claim 11, wherein the anode further includes an electroactive redox mediator to interface an active site of the catalyst with the surface of the anode.

14. The biofuel cell system of claim 11, wherein the cathode further includes an enzyme to facilitate the reduction of the oxygenated substance in the biological fluid to form the second product, the enzyme attached to the surface of the cathode by at least one of: (i) the enzyme is encased in a porous scaffold structure formed of a conducting polymer on the surface of the cathode, (ii) the enzyme is covalently bound to the surface of the cathode, (iii) the enzyme is entrapped in a selectively permeable membrane coupled to the surface of the cathode, or (iv) the enzyme is electrostatically bound to the surface of the cathode.

15. The biofuel cell system of claim 11, wherein the cathode includes an electroactive redox mediator to interface an active site of the enzyme with the surface of the cathode, the electroactive redox mediator facilitating the transfer of electrons from the cathode to the active site of the enzyme.

16. The biofuel cell system of claim 11, wherein the power storage module further includes a voltage regulator electrically coupled to the electrical storage unit and the electrical outlet to maintain a constant voltage level of the electrical energy.

17. The biofuel cell system of claim 11, wherein the power storage module further includes a power inverter electrically coupled to the electrical storage unit and the electrical outlet to convert the stored electrical energy from DC to AC electrical energy.

18. A method to fabricate a biofuel cell, comprising:
depositing an electrically conductive ink on a substrate to form an anode electrode and a cathode electrode adjacent to and separated from one another, the depositing including printing the ink on a stencil placed over the substrate, the stencil including a patterned region configured in a design of the anode and the cathode to allow transfer of the ink on the substrate, and the stencil inhibiting transfer of the ink in areas outside the patterned region; and
curing the electrically conductive ink to produce a biofuel cell device.

19. The method of claim 18, further comprising:
forming an electrically conductive layer under the anode electrode and cathode electrode by printing an ink of an electrically conductive material on a first stencil placed over the substrate, the first stencil including a printing region configured in a first design of conduit wires connecting to each of the anode and the cathode, the printing region allowing transfer of the ink on the substrate, and the first stencil inhibiting transfer of the ink in areas outside the printing region; and
curing the electrically conductive ink to produce a biofuel cell device.

20. The method of claim 18, further comprising:
depositing an electrically insulative ink on the substrate to form an insulative layer that exposes the anode electrode and the cathode electrode, the depositing including printing the electrically insulative ink on a second stencil placed over the substrate, the second stencil including a printing region configured in a second design to allow transfer of the ink on the substrate, the second stencil inhibiting transfer of the ink in areas outside the printing region; and
curing the electrically insulative ink.

21. The method of claim 18, further comprising depositing carbon nanotubes to the surface of at least one of the anode electrode or the cathode electrode.

22. The method of claim 18, further comprising:
depositing an enzyme catalyst to the surface of at least one of the anode electrode or the cathode electrode,
wherein the depositing includes performing at least one of:
(i) encasing the enzyme catalyst in a porous scaffold structure formed of a conducting polymer on the surface of the electrode,
(ii) covalently binding the enzyme catalyst to the surface of the electrode,
(iii) entrapping the enzyme catalyst in a selectively permeable membrane coupled to the surface of the electrode, or
(iv) electrostatically binding the enzyme catalyst to the surface of the electrode.

23. The method of claim 22, further comprising depositing an electroactive redox mediator to the surface of at least one of the anode electrode or the cathode electrode, wherein the electroactive redox mediator facilitates the transfer of electrons between the electrode and the active site of the enzyme catalyst.

24. The device of claim 2, wherein the substrate is structured to adhere to the skin of a user, and
wherein the load includes an anode electrode interface component and a cathode electrode interface component formed on the substrate and electrically coupled to the anode and the cathode, respectively, via electrical interconnects.

25. The device of claim 24, wherein the substrate includes a paper material formed of a paper base layer and releasing agent layer, the anode and the cathode formed on the releasing agent layer of the substrate.

* * * * *